(12) United States Patent
Ito et al.

(10) Patent No.: US 6,861,425 B2
(45) Date of Patent: Mar. 1, 2005

(54) BENZIMIDAZOLE COMPOUNDS AS ORL1-RECEPTOR AGONISTS

(75) Inventors: Fumitaka Ito, Chita-Gun (JP); Hirohide Noguchi, Chita-Gun (JP); Yoriko Ohashi, Chita-Gun (JP); Hirohisa Shimokawa, Chita-Gun (JP)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/753,954

(22) Filed: Jan. 3, 2001

(65) Prior Publication Data

US 2002/0049212 A1 Apr. 25, 2002

Related U.S. Application Data

(60) Provisional application No. 60/174,542, filed on Jan. 5, 2000.

(51) Int. Cl.$^7$ .................. C07D 487/08; C07D 401/14; C07D 403/14; C07D 401/04; A61K 31/496
(52) U.S. Cl. .............. 514/235.8; 514/252.13; 514/316; 514/322; 544/124; 544/364; 546/187; 546/199
(58) Field of Search ............... 546/187, 199; 544/124, 364; 514/252.13, 235.8, 316, 322

(56) References Cited

U.S. PATENT DOCUMENTS

| 3,318,900 A | 5/1967 | Janssen ............... 260/294 |
| 3,963,727 A | 6/1976 | Ueno et al. ............ 260/293 |
| 6,172,067 B1 * | 1/2001 | Ito et al. ............... 514/252.13 |

FOREIGN PATENT DOCUMENTS

| EP | 0990653 | 4/2000 |
| WO | WO9740035 | 10/1997 |
| WO | WO9854168 | 12/1998 |
| WO | WO0008013 | 2/2000 |

OTHER PUBLICATIONS

Patent Abstract of Japan, vol. 013, No 249 (C–605), (Jun. 9, 1989) (JP 01 056617 A, Mar. 3, 1989).
Patent Abstract of Japan, vol. 1999, No. 03, (Mar. 31, 1999) (JP 10 330377 A, Dec. 15, 1998).

* cited by examiner

*Primary Examiner*—Bruck Kifle
(74) *Attorney, Agent, or Firm*—Charles W. Ashbrook; David R. Kurlandsky; R. F. Waldron

(57) ABSTRACT

A compound of the formula:

(I)

or a pharmaceutically acceptable salt thereof, wherein $R^1$ is unsubstituted, mono-, di- or tri-substituted $(C_3-C_{11})$ cycloalkyl or $(C_3-C_{11})$cycloalkenyl or the like, A is unsubstituted $(C_1-C_7)$alkyl or $(C_2-C_5)$alkenyl, hydroxy-$(C_1-C_4)$ alkyl, $(C_1-C_4)$alkoxy-$(C=O)$, or unsubstituted, mono-, di- or tri-substituted aryl, or aromatic-heterocyclic or the like, M is a covalent bond O, S, NH or the like, Y is 4- to 12-membered bicyclic-carbocyclic rings or 4- to 12-membered bicyclic-heterocyclic rings, or 5- to 17 membered spirocarbocyclic rings or 5- to 17-membered spiroheterocyclic rings or the like, $Z^1$, $Z^2$, $Z^3$ and $Z^4$ are hydrogen or the like, is disclosed. These compounds have ORL1-receptor agonist activity, and are thus useful as analgesics or the like in mammalian subjects.

8 Claims, No Drawings

BENZIMIDAZOLE COMPOUNDS AS ORL1-RECEPTOR AGONISTS

This application claims the benefit of U.S. provisional patent application Ser. No. 60/174,542, filed Jan. 5, 2000.

TECHNICAL FIELD

This invention relates to benzimidazole compounds, and salts thereof, pharmaceutical compositions containing them and methods of treatment comprising the administration of those compounds. The present invention further relates to methods for preparing those compounds and intermediate compounds useful in the processes. The compounds of the present invention have activity as selective ORL1-receptor agonists, and as such, are useful in treating or preventing disorders or medical conditions selected from pain, inflammatory diseases and the like.

BACKGROUND ART

In spite of their usefulness as analgesics, opioids, such as morphine and heroin, have serious side effects such as euphoria, respiratory depression or constipation. Further, treatment regimens incorporating multiple dosages of opioid compounds risk patient addiction to those drugs. Thus, there has been a long-felt need to provide analgesic compounds without those side effects.

A considerable number of pharmacological and biochemical studies have been carried out in order to identify opioid receptors and their endogenous ligands to prepare peptide and non-peptide opioid ligands for the receptors. In the recent past, amino acid sequences of mu- ($\mu$-), delta ($\delta$-) and kappa ($\kappa$-) opioid receptor subtypes have been identified and reported. A further receptor subtype the ORL1-receptor has been identified and termed ORL1-receptor, and the isolation and structure of its endogenous agonist have been reported (Meunier, J.-C et al., *Nature*, Vol. 377, pp. 532–535 (1995)). The agonist compounds for ORL1-receptor are suggested to be effective in treating neurogenic inflammation (*Tips*, Vol. 18, pp. 293–300 (1997)), and to be potent analgesics with fewer psychological side effects and risk of patient addiction (D. Julius, *Nature*, Vol. 377, p. 476 (1995)).

WO 00/08013 discloses 2-substituted benzimodazole compounds as ORL1-agonists.

BRIEF DISCLOSURE OF THE INVENTION

The present invention provides a compound of the following formula:

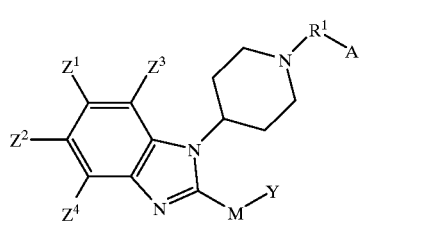

(I)

or a salt thereof, wherein $R^1$ is selected from the group consisting of ($C_3$–$C_{11}$) cycloalkyl, ($C_6$–$C_{16}$)bicycloalkyl, ($C_6$–$C_{16}$) tricycloalkyl and ($C_8$–$C_{16}$)tetracycloalkyl, wherein said groups are partially saturated, fully saturated or fully unsaturated and are optionally substituted with 1 to 3 substituents independently selected from the group consisting of halo, hydroxy, ($C_1$–$C_5$)alkyl and ($C_3$–$C_7$) cycloalkyl;

A is attached to the same carbon atom of $R^1$ that is also attached to the nitrogen atom of the piperidine ring, and is selected from the group consisting of ($C_1$–$C_7$)alkyl optionally substituted with 1 to 3 halo; ($C_2$–$C_5$)alkenyl; ($C_2$–$C_5$)alkynyl; phenyl-($C_1$–$C_5$)alkyl optionally substituted at the phenyl moiety with 1 to 3 substituents; hydroxy-($C_1$–$C_4$)alkyl; ($C_1$–$C_4$)alkoxy-(C=O); aryl optionally substituted with 1 to 3 substituents; and an aromatic or non-aromatic heterocyclic ring comprising four to ten ring atoms wherein one to four ring atoms are independently selected from nitrogen, oxygen and sulfur and said aromatic or non-aromatic heterocyclic ring is optionally substituted with 1 to 3 substituents, and the substituents attached to said phenyl moiety in the phenyl-($C_1$–$C_5$)alkyl, aryl or heterocyclic ring is independently selected from the group consisting of halo; hydroxy; ($C_1$–$C_4$)alkyl optionally substituted with 1 to 3 halo; ($C_1$–$C_4$)alkoxy optionally substituted with 1 to 3 halo; ($C_1$–$C_4$)alkyl-CO—; phenyl; benzyl; —CHO; cyano; ($C_1$–$C_4$)alkyl-CO—; $NH_2$—CO—; $NH_2$—$CH_2$—; amino; ($C_1$–$C_4$)alkyl-NH—; di[($C_1$–$C_4$) alkyl]-N—; ($C_1$–$C_4$)alkyl-CO—NH—; ($C_1$–$C_4$)alkyl-NH—CO—; hydrazino; azido; ureido; amidino; guanidino; oxo and =N—OH;

M is selected from the group consisting of a single covalent bond, $CH_2$, O, S, SO, $SO_2$, CO, NH, N[($C_1$–$C_6$)alkyl], CONH and NHCO;

Y is selected from the following:

(a) 4- to 12-membered bicyclic-carbocyclic rings wherein said bicyclic-carbocyclic rings are optionally substituted with 1 to 6 substituents independently selected from the group consisting of halo, hydroxy, ($C_1$–$C_4$) alkyl optionally substituted with 1 to 3 halo; ($C_1$–$C_4$) alkoxy optionally substituted with 1 to 3 halo; ($C_1$–$C_4$) alkyl-CO—; phenyl; benzyl; —CHO; cyano; ($C_1$–$C_4$) alkyl-CO—; $NH_2$—CO—; $NH_2$—$CH_2$—; amino; ($C_1$–$C_4$)alkyl-NH—; di[($C_1$–$C_4$)alkyl]-N—; ($C_1$–$C_4$) alkyl-CO—NH—; ($C_1$–$C_4$)alkyl-NH—CO—; hydrazino; azido; ureido; amidino; guanidino; oxo and =N—OH, wherein the optionally substituted ($C_1$–$C_4$) alkyl are attached to the carbon or nitrogen atoms and other substituents are attached to the carbon atoms in the bicyclic-heterocyclic ring; with the proviso that said bicyclic-carbocyclic ring is not a benzofused ring;

(b) 4- to 12-membered bicyclic-heterocyclic rings wherein 1 to 6 ring atoms are independently selected from nitrogen, oxygen and sulfur wherein said bicyclic-heterocyclic rings are optionally substituted with 1 to 6 substituents independently selected from the group consisting of halo; hydroxy; ($C_1$–$C_4$)alkyl optionally substituted with 1 to 3 substituents independently selected from halo, hydroxy, ($C_1$–$C_3$)alkyl-$SO_2NH_2$— and $NH_2C$(=O)NH—; ($C_1$–$C_4$)alkoxy optionally substituted with 1 to 3 halo; ($C_1$–$C_4$)alkyl-CO—; aryl optionally substituted with 1 to 3 substituents independently selected from halo, ($C_1$–$C_4$)alkyl optionally substituted with 1 to 3 halo and ($C_1$–$C_4$)alkoxy; benzyl optionally substituted with 1 to 3 substituents independently selected from halo, ($C_1$–$C_4$)alkyl optionally substituted with 1 to 3 halo and ($C_1$–$C_4$)alkoxy; —CHO; cyano; ($C_1$–$C_4$)alkyl-CO—; $NH_2$—CO—; $NH_2$—$CH_2$—; amino; ($C_1$–$C_4$)alkyl-NH—; di[($C_1$–$C_4$)alkyl]-N—; ($C_1$–$C_4$)alkyl-CO—NH—; ($C_1$–$C_4$)alkyl-NH—CO—; hydrazino; azido; ureido; amidino; guanidino; oxo and =N—OH, wherein the optionally substituted ($C_1$–$C_4$)alkyl are attached to the carbon or nitrogen atoms and other substituents are attached to the carbon atoms in the bicyclic-heterocyclic ring; with the proviso that said bicyclic-heterocyclic ring is not a benzofused ring;

(c) 5- to 17 membered spirocarbocyclic rings wherein said spirocarbocyclic rings are optionally substituted with 1 to 6 substituents independently selected from the group consisting of halo; hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—; phenyl; benzyl; —CHO; cyano; $(C_1-C_4)$alkyl-CO—; $NH_2$—CO—; $NH_2$—$CH_2$—; amino; $(C_1-C_4)$alkyl-NH—; di[$(C_1-C_4)$alkyl]-N—; $(C_1-C_4)$alkyl-CO—NH—; $(C_1-C_4)$alkyl-NH—CO—; hydrazino; azido; ureido; amidino; guanidino; oxo and =N—OH;

(d) 5- to 17-membered spiroheterocyclic rings wherein 1 to 6 ring atoms are independently selected from nitrogen, oxygen and sulfur, wherein said spiroheterocyclic rings are optionally substituted with 1 to 6 substituents independently selected from the group consisting of halo; hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—; phenyl; benzyl; —CHO; cyano; $(C_1-C_4)$alkyl-CO—; $NH_2$—CO—; $NH_2$—$CH_2$—; amino; $(C_1-C_4)$alkyl-NH—; di-[$(C_1-C_4)$alkyl]N—; $(C_1-C_4)$alkyl-CO—NH—; $(C_1-C_4)$alkyl-NH—CO—; hydrazino; azido; ureido; amidino; guanidino; oxo and =N—OH; and $Z^1$, $Z^2$, $Z^3$ and $Z^4$ are independently selected from the group consisting of hydrogen, halo, $(C_1-C_4)$alkyl optionally substituted with 1 to 3 halo; $(C_1-C_4)$alkoxy optionally substituted with 1 to 3 halo; $(C_1-C_4)$alkylsulfonyl; $(C_1-C_4)$alkyl-CO—; carboxy; $(C_1-C_4)$alkyl-COO—; amino; $NH_2CO$—; $(C_1-C_4)$alkyl-CO—NH—; $(C_1-C_4)$alkyl-$SO_2$—NH—; phenyl and naphthyl.

This invention also relates to a pharmaceutical composition for the treatment of a disorder or condition mediated by ORL1-receptor and its endogenous ligands in a mammal including a human, or for anesthetizing a mammal including a human, which comprises an effective amount of the compound of formula (I), or a pharmaceutically acceptable salt thereof, and a pharmaceutically acceptable carrier.

More specifically, this invention relates to a pharmaceutical composition for the treatment of a disorder or condition selected from the group consisting of neuropathic pain, inflammatory diseases, inflammation-related hyperalgesia, eating disorders (e.g., in obesity), arterial blood pressure disorders (i.e., hypertension or hypotension), tolerance to narcotic analgesics such as morphine, dependence on narcotic analgesics such as morphine, anxiety, stress disorders, psychic trauma, schizophrenia, Parkinson's disease, chorea, depressant, Alzheimer's disease, dementias, epilepsy and convulsions, useful as analgesics (for acute, chronic or neuropathic pain), anesthetics, neuroprotective agent or analgesic enhancers, or useful for controlling water balance (e.g., in diabetes insipidus and polyuria), hearing regulation, controlling sodium ion excretion, ameliorating brain function, comprising an amount of a compound of formula (I), or a pharmaceutically acceptable salt thereof that is effective in treating such disorder or condition in a mammal including a human, and a pharmaceutically acceptable carrier.

This invention also relates to a method of treating a disorder or condition, or anesthetizing a mammal including a human, where the treatment or anesthetization of which can be effected or facilitated by activating ORL1-receptor in a mammal, including a human, comprising administering to a mammal in need of such treatment an effective amount of a compound of formula (I) or a pharmaceutically acceptable salt thereof.

More specifically, this invention relates to a method for treating a disorder or condition in a mammal including a human, where the disorder or condition is selected from the group consisting of neuropathic pain, inflammatory diseases, inflammation-related hyperalgesia, eating disorder (e.g., in obesity), arterial blood pressure disorders (i.e., hypertension or hypotension), tolerance to narcotic analgesics such as morphine, dependence on narcotic analgesics such as morphine, anxiety, stress disorders, psychic trauma, schizophrenia, Parkinson's disease, chorea, depressant, Alzheimer's disease, dementias, epilepsy and convulsions, or for anesthetizing a mammal including a human, or for alleviating pain (e.g., acute, chronic and neuropathic pain), producing a neuroprotective effect, enhancing analgesic, controlling water balance (e.g., in diabetes insipidus and polyuria), hearing regulation, controlling sodium ion excretion or ameliorating brain function in a mammal including a human, comprising administering to said mammal an effective amount of a compound of formula (I) or a pharmaceutically acceptable salt thereof and a pharmaceutically acceptable carrier.

DETAILED DESCRIPTION OF THE INVENTION

The term "alkyl", as used herein, means a straight or branched saturated monovalent hydrocarbon radical including, but not limited to, methyl, ethyl, propyl, isopropyl, n-butyl, sec-butyl, tert-butyl and the like.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "$C_5$-$C_9$ alkenyl ring", as used herein, means a carbocyclic radical having at least one double bond including, but not limited to, cyclopentenyl, cyclohexenyl, cycloheptenyl, cyclooctenyl, cyclononenyl, cyclodecenyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "alkoxy", as used herein, means an O-alkyl group wherein "alkyl" is defined above.

The term "halo", as used herein, refers to F, Cl, Br or I, preferably F or Cl.

The term "aryl", as used herein, means a monocyclic or bicyclic aromatic carbocyclic ring system of 6–11 ring carbon atoms including, but not limited to, phenyl, naphthyl, indanyl, (1,2,3,4)-tetrahydronaphthyl, indenyl, isoindenyl and the like.

The term "aromatic or non-aromatic heterocyclic" or "heterocyclic", as used herein, unless otherwise indicated, includes aromatic and non-aromatic heterocyclic groups having four to ten ring atoms comprising one to four heteroatoms each selected from O, S and N. Such heterocyclic groups include those having a fused benzene ring optionally substituted with an oxo moiety. Examples of the aromatic and non-aromatic heterocyclic are azetidinyl, furyl, thienyl, pyrrolyl, pyrroldinyl, oxazolyl, isooxazolyl, thiazolyl, isothiazolyl, imidazolyl, pyrazolyl, triazolyl, furazanyl, tetrazolyl, pyranyl, thiinyl, pyridyl, piperidyl (or piperidinyl), piperidino, oxazinyl, morpholinyl, morphorino, thiamorpholino, thiazinyl, pyridazinyl, pyrimidinyl, pyrazinyl, piperazinyl, piperazino, triazinyl, benzofuranyl, isobenzofuranyl, benzothiophenyl, indolyl, isoindolyl, benzoxazolyl, benzothiazolyl, indazolyl, benzimidazolyl, chromanyl, isochromanyl, quinolyl, isoquinolyl, cinnolinyl, phthalazinyl, quinazolinyl and quinoxalinyl.

Preferred heterocyclics are four to six membered heterocyclic comprising one to two heteroatoms. Examples of the four to six membered heterocyclic include piperidyl, piperidino, piperazinyl, piperazino.

The term "tri- or tetra-cyclic ring" means hydrocarbon cyclic groups of 6 to 16 ring carbon atoms, having two to four rings therein, including, but not limited to, adamantane and tricyclo[5.2.1.0$^{2,6}$]decane and the like.

The term "4- to 12-membered bicyclic-carbocyclic ring", as used herein, means hydrocarbon cyclic groups of 4 to 12 ring carbon atoms, having two rings therein, including, but not limited to, decahydronaphthalene, bicyclo[2.2.1.] heptane, bicyclo[3.2.1 ]octane, bicyclo[3.3.1 ]nonane and the like.

The term "4- to 12-membered bicyclic-heterocyclic ring", as used herein, means 4- to 12-membered (preferably 6 to 10 membered) bicyclic heterocyclic moiety which consists of carbon atoms and 1 to 6 preferably 1 to 4) heteroatoms selected from the group consisting of N, O and S. Those bicyclic-heterocyclic rings do not include benzofuzed rings. Examples of such bicyclic-heterocyclic rings include, but not limited to, 3,8-diazabicyclo[3.2.1 ]octane, 2,5-diazabicyclo[2.2.1 ]heptane, hexahydropyrrolo[3,4-c] pyrrole, hexahydropyrrolo[3,4-b]pyrrole, 6-amino-3-azabicyclo[3.1.0]hexane, (8aS)-hexahydropyrrolo[1,2-a] pyrazine, octahydro-2H-pyrido[1,2-α]pyrazine, octahydro-6H-pyrido[1,2-a]pyrazin-6-one, octahydroimidazo[1,5-a] pyrazine, hexahydro[1,3]oxazolo[3,4-a]pyrazin-3-one, hexahydroimidazo[1,5-a]pyrazin-3(2H)-one, hexahydropyrrolo[1,2-a]pyrazin-6(2H)-one, hexahydro[1,3] oxazolo[3,4-a]pyrazine, octahydropyrrolo[3,4-b][1,4] oxazine, octahydro-1H-pyrrolo[3,4-b]pyridine, tetrahydropyrrolo[3,4-c]pyrrole-1,3 (2H,3aH)-dione, hexahydropyrrolo[3,4-c]pyrrol-1(2H)-one, octahydro-2H-benzimidazol-2-one, 2,5-diazabicyclo[2,2,2]octane, 8-azabicyclo[3,2,1]octane, decahydro[1,6]naphthyridine, octahydro-1H-pyrrolo[3,4-c]pyridine and the like.

The term "5- to 17-membered spirocarbocyclic ring", as used herein, means a 5- to 17-membered (preferably 5- to 11-membered) cycloalkyl moiety comprising two cycloalkyl rings bonded to each other through one carbon atom in the cycloalkyl moiety, wherein each cycloalkyl ring comprises at least three ring carbon atoms. Examples of such spirocarbocyclic rings include, but not limited to, spiro[5,5] undecan, spiro[4,5]decan, spiro[3,4]octane and the like. Such spirocyclic groups include those having a fused aromatic ring such as benzene or (C$_4$–C$_6$)carbocyclic ring.

The term "5- to 17-membered spiroheterocyclic ring", as used herein, means a 5- to 17-membered (preferably 10- to 15-membered) heterocyclic moiety comprising one carbocyclic ring and heterocyclic ring, or two heterocyclic rings, wherein the carbocyclic ring and heterocyclic ring or the two heterocyclic rings are bonded to each other through one carbon atom in the cycloalkyl moiety. The carbocyclic ring in the spiroheterocyclic ring comprises at least three carbon ring atoms. The heterocyclic ring in the spiroheterocyclic ring comprises at lease three ring atoms, and at least one of the ring atoms are independently selected from nitrogen, oxygen and sulfur. In case the spiroheterocyclic ring comprises two heterocyclic rings, then the ring atoms in each ring are independently selected from carbon, nitrogen, oxygen and sulfur. Examples of such spiroheterocyclic rings include, but not limited to, 1,4-diazaspiro[5,5]undecane, 8,8,10,10-tetramethyl-1,4-diazaspiro[5,5]undecane, 1,4-diazaspiro[5,5]undecan-2-one and the like.

Such spiro heterocyclic groups include those having a fused aromatic ring such as cyclohexane, benzene or pyridine.

The term "N[(C$_1$–C$_6$)alkyl]", as used herein, means the group represented by the following formula.

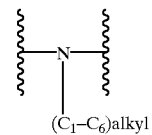

The "A" group is attached to the carbon atom of R$^1$, which is attached to the nitrogen atom of the piperidine ring as indicated bellow.

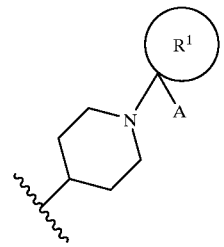

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred group of compounds of the present invention includes compounds of formula (I) wherein
   R$^1$ is (C$_3$–C$_{11}$)cycloalkyl wherein said (C$_3$–C$_{11}$) cycloalkyl, wherein said cycloalkyl is partially saturated, fully saturated or fully unsaturated and is optionally substituted with 1 to 3 substituents independently selected from the group consisting of halo, hydroxy, (C$_1$–C$_5$)alkyl and (C$_3$–C$_7$)cycloalkyl;
   A is attached to the same carbon atom of R$^1$ that is also attached to the nitrogen atom of the piperidine ring, and is selected from the group consisting of (C$_1$–C$_7$)alkyl optionally substituted with 1 to 3 halo; (C$_2$–C$_5$)alkenyl; (C$_2$–C$_5$)alkynyl; hydroxy-(C$_1$–C$_4$)alkyl; (C$_1$–C$_4$) alkoxy-(C=O); aryl optionally substituted with 1 to 3 substituents; and an aromatic or non-aromatic heterocyclic ring comprising four to six ring atoms wherein one to two ring atoms are independently selected from nitrogen, oxygen and sulfur and said aromatic or non-aromatic heterocyclic ring is optionally substituted with 1 to 3 substituents; and the substituents attached to said aryl or heterocyclic ring are independently selected from halo; (C$_1$–C$_4$)alkyl optionally substituted with 1 to 3 halo; (C$_1$–C$_4$)alkoxy optionally substituted with 1 to 3 halo; (C$_1$–C$_4$)alkyl-CO—; NH$_2$—CO—; NH$_2$—CH$_2$—; amino; (C$_1$–C$_4$)alkyl-NH—; di[(C$_1$–C$_4$)alkyl]-N—; (C$_1$–C$_4$)alkyl-CO—NH— and (C$_1$–C$_4$)alkyl-NH—CO—;

M is selected from group consisting of a covalent bond, $CH_2$, O, S, $SO_2$, CO, NH, $N[(C_1-C_6)alkyl]$, CONH and NHCO;
Y is selected from the following:
(a) bicyclic rings represented by formula Y1:

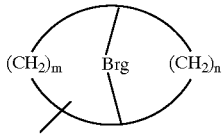

wherein m and n are independently 1, 2, 3 or 4; Brg is selected from $(CH_2)_p$ wherein p is 0, 1 or 2, and $N-(C_1-C_4)alkyl$; and Y1 is optionally substituted with 1 to 4 substituents independently selected from the group consisting of hydroxy; $(C_1-C_4)alkyl$ optionally substituted with 1 to 3 halo; $(C_1-C_4)alkoxy$ optionally substituted with 1 to 3 halo; $(C_1-C_4)alkyl-CO-$; phenyl; benzyl; $(C_1-C_4)alkyl-CO-$; $NH_2-CO-$; $NH_2-CH_2-$; amino; $(C_1-C_4)alkyl-NH-$; $di[(C_1-C_4)alkyl]-N-$; $(C_1-C_4)alkyl-CO-NH-$; $(C_1-C_4)alkyl-NH-CO-$; oxo and $=N-OH$;

(b) 6- to 10-membered bicyclic-heterocyclic rings, containing 1 to 4 hetero atoms in the ring, represented by formula Y2, Y3 or Y4:

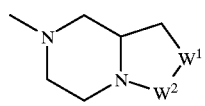

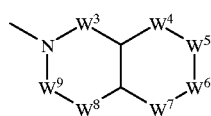

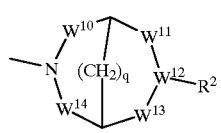

wherein
$W^1$ is selected from $CH_2$, $CH_2CH_2$, O, S and NH;
$W^2$ is selected from $CH_2$, O, S, NH and C=O;
$W^3$ is selected from a covalent bond, $CH_2$, O, S, NH and C(=O)-NH;
$W^4$ is selected from a covalent bond, $CH_2$, O, S and NH;
$W^5$ is selected from a covalent bond, $CH_2$, $CH(CH_2OH)$, $CH(CH_2NHSO_2CH_3)$, $CH(CH_2NHC(=O)NH_2)$, $CH_2CH_2$, O, S, NH and C(=O);
$W^6$ is selected from $CH_2$, O, S, NH and $N[(C_1-C_4)alkyl]$;
$W^7$ is selected from a covalent bond, $CH_2$, O, S, NH and C(=O);
$W^8$ is selected from a covalent bond, $CH_2$, O, S and NH;
$W^9$ is selected from a covalent bond, $CH_2$, O, S, NH $CH_2CH_2$ and C(=O);
$W^{10}$, $W^{11}$, $W^{13}$ and $W^{14}$ are independently selected from covalent bond, $CH_2$, O, S, and NH;
$W^{12}$ is selected from CH and N;
q is 1 or 2; and
$R^2$ is selected from hydrogen, $(C_1-C_4)alkyl$ and amino; and
said bicyclic-heterocyclic rings of formula Y2, Y3 or Y4 is optionally substituted with 1 to 4 substituents independently selected from the group consisting of halo; hydroxy; $(C_1-C_4)alkyl$ optionally substituted with 1 to 3 halo; $(C_1-C_4)alkoxy$ optionally substituted with 1 to 3 halo; $(C_1-C_4)alkyl-CO-$; ayrl optionally substituted with 1 to 3 substituents independently selected from halo, $(C_1-C_4)alkyl$ optionally substituted with 1 to 3 halo and $(C_1-C_4)alkoxy$; benzyl optionally substituted with 1 to 3 substituents independently selected from halo, $(C_1-C_4)alkyl$ optionally substituted with 1 to 3 halo and $(C_1-C_4)alkoxy$; $-CHO$; cyano; $(C_1-C_4)alkyl-CO-$; $NH_2-CO-$; $NH_2-CH_2-$; amino; $(C_1-C_4)alkyl-NH-$; $di[(C_1-C_4)alkyl]-N-$; $(C_1-C_4)alkyl-CO-NH-$; $(C_1-C_4)alkyl-NH-CO-$; oxo and $=N-OH$;

(c) spirocarbocyclic rings represented by formula Y5:

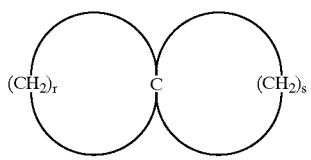

wherein r and s are independently 2, 3, 4 or 5; and said spirocarbocyclic ring or formula Y5 is optionally substituted with 1 to 4 substituents independently selected from the group consisting of hydroxy; $(C_1-C_4)alkyl$ optionally substituted with 1 to 3 halo; $(C_1-C_4)alkoxy$ optionally substituted with 1 to 3 halo; $(C_1-C_4)alkyl-CO-$; phenyl; benzyl; $(C_1-C_4)alkyl-CO-$; $NH_2-CO-$; $NH_2-CH_2-$; amino; $(C_1-C_4)alkyl-NH-$; di $[(C_1-C_4)alkyl]-N-$; $(C_1-C_4)alkyl-CO-NH-$; $(C_1-C_4)alkyl-NH-CO-$; oxo and $=N-OH$; and either of monocyclic carbocyclic ring in Y5 is optionally fused to a benzene or $(C_4-C_6)carbocyclic$ ring;

(d) 10- to 15-membered spiroheterocyclic rings, containing 1 to 4 hetero atoms in the ring, represented by formula Y6:

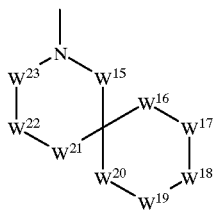

wherein
$W^{15}$, $W^{16}$, $W^{17}$, $W^{18}$, $W^{19}$, $W^{20}$ and $W^{23}$ are independently selected from the group consisting of a covalent bond $CH_2$, O, S and NH;
$W^{21}$ is selected from the group consisting of a covalent bond $CH_2$, O, S, NH and $N[(C_1-C_4)alkyl]$;
$W^{22}$ is selected from the group consisting of a covalent bond $CH_2$, O, S, NH and C(=O);
said spiroheterocyclic ring of formula Y6 is optionally substituted with 1 to 4 substituents independently selected from the group consisting of halo; hydroxy;

($C_1$–$C_4$)alkyl optionally substituted with 1 to 3 halo; ($C_1$–$C_4$)alkoxy optionally substituted with 1 to 3 halo; ($C_1$–$C_4$)alkyl-CO—; phenyl; benzyl; —CHO; cyano; ($C_1$–$C_4$)alkyl-CO—; $NH_2$—CO—; $NH_2$—$CH_2$—; amino; ($C_1$–$C_4$)alkyl-NH—; di[($C_1$–$C_4$)alkyl]-N—; ($C_1$–$C_4$)alkyl-CO—NH—; ($C_1$–$C_4$)alkyl-NH—CO—; hydrazino; azido; ureido; amidino; guanidino; oxo and =N—OH; and optionally fused to a cyclohexane, benzene or pyridine ring; and $Z^1$, $Z^2$, $Z^3$ and $Z^4$ are independently selected from the group consisting of hydrogen and halo.

A further preferred group of compounds of the present invention includes compounds of formula (I) wherein $R^1$ is selected from the group consisting of ($C_3$–$C_{11}$) cycloalkyl;

A is attached to the carbon atom of $R^1$, which is attached to the nitrogen atom of the piperidine ring, and selected from the group consisting of ($C_1$–$C_7$)alkyl, hydroxy-($C_1$–$C_2$)alkyl, ($C_1$–$C_4$)alkoxy-(C=O), ($C_2$–$C_5$) alkenyl, phenyl and naphthyl;

M is selected from the group consisting of a covalent bond, $CH_2$, O, $SO_2$, CO, NH, N[($C_1$–$C_6$)alkyl], and NHCO;

Y is selected from bicyclic rings represented by formula Y1; 6- to 10-membered bicyclic-heterocyclic rings, containing 1 to 4 hetero atoms in the ring, represented by formula Y2, Y3 and Y4; and 10- to 15-membered spiroheterocyclic rings, containing 1 to 4 hetero atoms in the ring, represented by formula Y6:

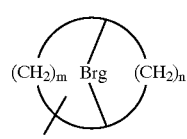

Y1

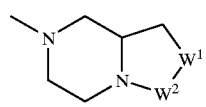

Y2

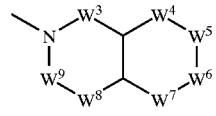

Y3

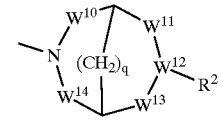

Y4

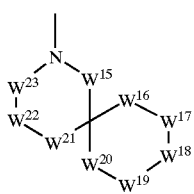

Y6 wherein
m and n are independently 1, 2, 3 or 4;
Brg is N-($C_1$–$C_4$)alkyl;
$W^1$ is selected from $CH_2$, $CH_2CH_2$, O and NH;
$W^2$ is selected from $CH_2$ and C=O;

$W^3$ is selected from a covalent bond, $CH_2$ and C(=O)—NH;

$W^4$ is selected from a covalent bond, $CH_2$ and O;

$W^5$ is selected from a covalent bond, $CH_2$, CH($CH_2OH$), CH($CH_2NHSO_2CH_3$), CH($CH_2NHC(=O)NH_2$), $CH_2CH_2$ and C(=O);

$W^6$ is selected from $CH_2$, NH and N[($C_1$–$C_4$)alkyl];

$W^7$ is selected from a covalent bond, $CH_2$ and C(=O);

$W^8$ is selected from a covalent bond and $CH_2$;

$W^9$ is selected from a covalent bond, $CH_2$, $CH_2CH_2$ and C(=O);

$W^{10}$, $W^{11}$, $W^{13}$ and $W^{14}$ are independently selected from a covalent bond and $CH_2$;

$W^{12}$ is selected from CH and N;

q is 1 or 2;

$R^2$ is selected from hydrogen, ($C_1$–$C_4$)alkyl and amino;

$W^{15}$, $W^{16}$, $W^{17}$, $W^{18}$, $W^{19}$, $W^{20}$ and $W^{23}$ are independently selected from the group consisting of a covalent bond and $CH_2$;

$W^{21}$ is selected from the group consisting of a covalent bond $CH_2$, NH and N[($C_1$–$C_4$)alkyl];

$W^{22}$ is selected from the group consisting of a covalent bond $CH_2$ and C(=O);

said group of formula of Y2, Y3 or Y4 is optionally substituted with 1 to 4 substituent independently selected from the group consisting of ($C_1$–$C_4$)alkyl; aryl optionally substituted with 1 to 3 substituents independently selected from halo, ($C_1$–$C_4$)alkyl optionally substituted with 1 to 3 halo and ($C_1$–$C_4$) alkoxy; and benzyl optionally substituted with 1 to 3 substituents independently selected from halo, ($C_1$–$C_4$)alkyl optionally substituted with 1 to 3 halo and ($C_1$–$C_4$)alkoxy; and said group of formula Y6 is optionally fused to a cyclohexane, benzene or pyridine ring; and optionally substituted with 1 to 4 substituents independently selected from the group consisting of ($C_1$–$C_4$) alkyl, ($C_1$–$C_4$)alkoxy and aryl;

$Z^1$ and $Z^2$ are independently selected from the group consisting of hydrogen and halo; and $Z^3$ and $Z^4$ are both hydrogen.

A further preferred group of compounds of the present invention includes compounds of formula (I) wherein $R^1$ is ($C_6$–$C_{10}$)cycloalkyl;

A is attached to the carbon atom of $R^1$, which is attached to the nitrogen atom of the piperidine ring, and is selected from the group consisting of ($C_1$–$C_7$)alkyl and, phenyl 1;

M is selected from group consisting of a covalent bond, $CH_2$, O, $SO_2$, CO, NH, N[($C_1$–$C_6$)alkyl] and NHCO, Y is selected from:

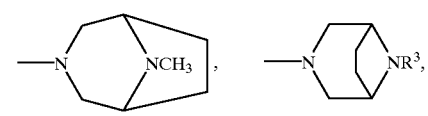

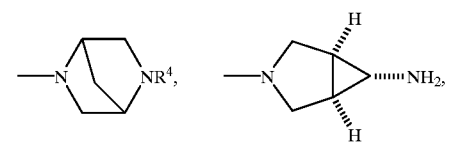

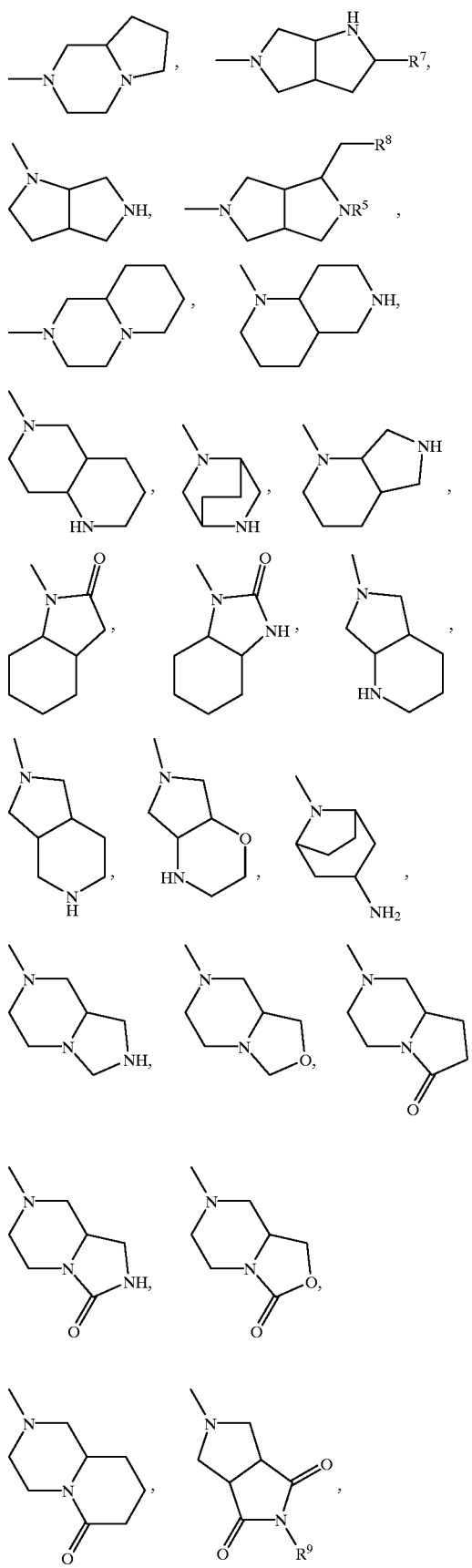

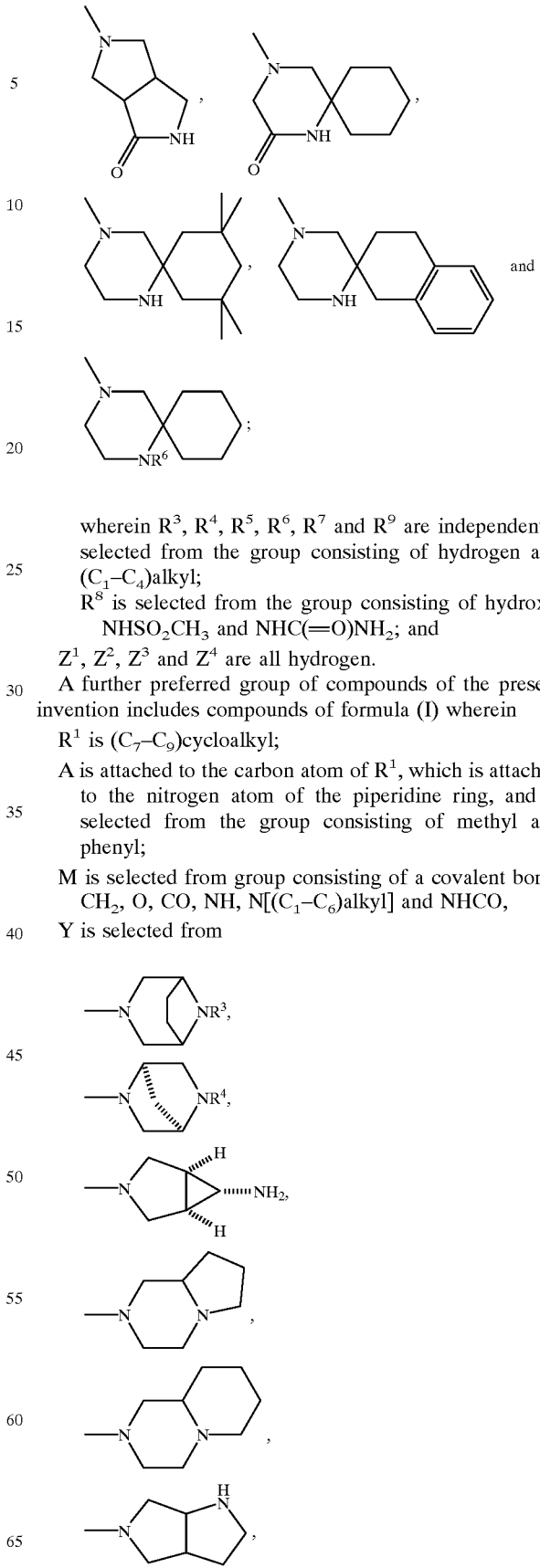

wherein $R^3$, $R^4$, $R^5$, $R^6$, $R^7$ and $R^9$ are independently selected from the group consisting of hydrogen and $(C_1-C_4)$alkyl;

$R^8$ is selected from the group consisting of hydroxy, $NHSO_2CH_3$ and $NHC(\!\!=\!\!O)NH_2$; and $Z^1$, $Z^2$, $Z^3$ and $Z^4$ are all hydrogen.

A further preferred group of compounds of the present invention includes compounds of formula (I) wherein $R^1$ is $(C_7-C_9)$cycloalkyl;

A is attached to the carbon atom of $R^1$, which is attached to the nitrogen atom of the piperidine ring, and is selected from the group consisting of methyl and phenyl;

M is selected from group consisting of a covalent bond, $CH_2$, O, CO, NH, $N[(C_1-C_6)alkyl]$ and NHCO, Y is selected from

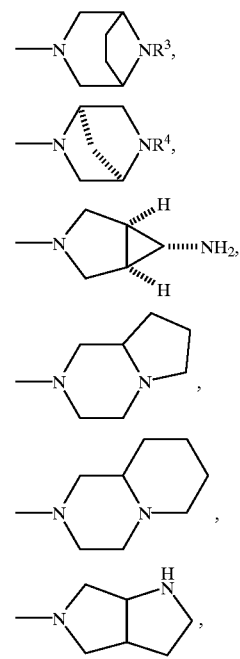

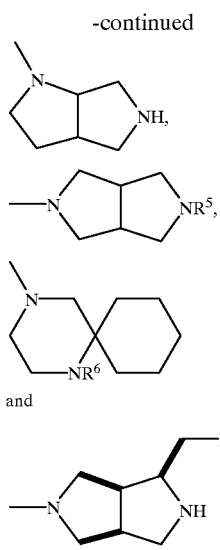

and wherein $R^3$, $R^4$, $R^5$ and $R^6$ are independently selected from the group consisting of hydrogen and ($C_1$–$C_4$) alkyl; and $Z^1$, $Z^2$, $Z^3$ and $Z^4$ are all hydrogen.

Preferred individual compounds of this invention are

4-{1-[1-(1-methylcyclooctyl)-4-piperidinyl]-1H-benzimidazole-2-yl}-1,4-diazaspiro[5.5]undecane;

2-hexahydropyrrolo[3,4-c]pyrrol-2(1H)-yl-1-[1-(1-methylcyclooctyl)-4-piperidinyl]-1H-benzimidazole;

2-(3,8-Diazabicyclo[3.2.1]oct-3-yl)-[1-(1-methylcyclooctyl)-4-piperidinyl]-1H-benzimidazole; and N-[(1SR,3aRS,6aSR)-5-{1-[1-(1-Methylcyclooctyl)-4-piperidinyl]-1H-benzimidazol-2-yl}octahydropyrrolo[3,4-c]pyrrole-1-ylmethyl]urea; and a salt thereof.

General Synthesis

The following reaction Schemes illustrate the preparation of the compounds of the present invention. Unless otherwise indicated, $R^1$, A, M, Y, and $Z^1$ to $Z^4$ in the reaction Schemes and discussion that follow are defined as above.

The ORL1 agonist compounds of Formula (I) of this invention may be prepared according to the following methods.

In the reaction schemes appearing below, a substituent represented by A of compounds of the formulae (V), (Ia), (VI), (VII), (IX), (X), (XIII), (XIV) and (XVI) is attached to the carbon atom in $R^1$, which is attached to the nitrogen atom of the piperidine ring. In compounds of formulae (IV), (XII) and (XVI), the cyano group is also attached to the carbon atom in $R^1$, which is attached to the nitrogen atom in the piperidine ring. In compounds of formula (XIV), A is attached to the same carbon atom of $R^1$ where the amino group is attached.

In a desired reaction step of the processes described hereafter, amino (or imino) protection and removal of the amino protecting groups with reactants and reagents used may be carried out according to known procedures such as those described in Protective Groups in Organic Synthesis edited by T. W. Greene et al. (John Wiley & Sons, 1991). Typical amino protecting groups include benzyl, $C_2H_5CO_2$— and t-ButCO$_2$— represented as t-Boc or Boc. For example, amino protection with Boc may be carried out by a reaction of a reactant or reagent used and (Boc)$_2$O in the presence of a base such as triethylamine in a reaction inert solvent such as dichloromethane. The Boc group thus introduced may be subsequently removed in an appropriate reaction step. Removal of Boc may be conducted by reduction in the presence of a metal catalyst such as palladium-carbon under hydrogen or treating the N-protected compound with a protonic acid such as hydrochloric acid in a reaction inert solvent such as an alkanol.

Scheme 1 illustrates an embodiment of preparation process for a compound of formula (I) through a nucleophilic substitution reaction of a compound of formula (Ia) wherein L is a leaving group.

Scheme 1

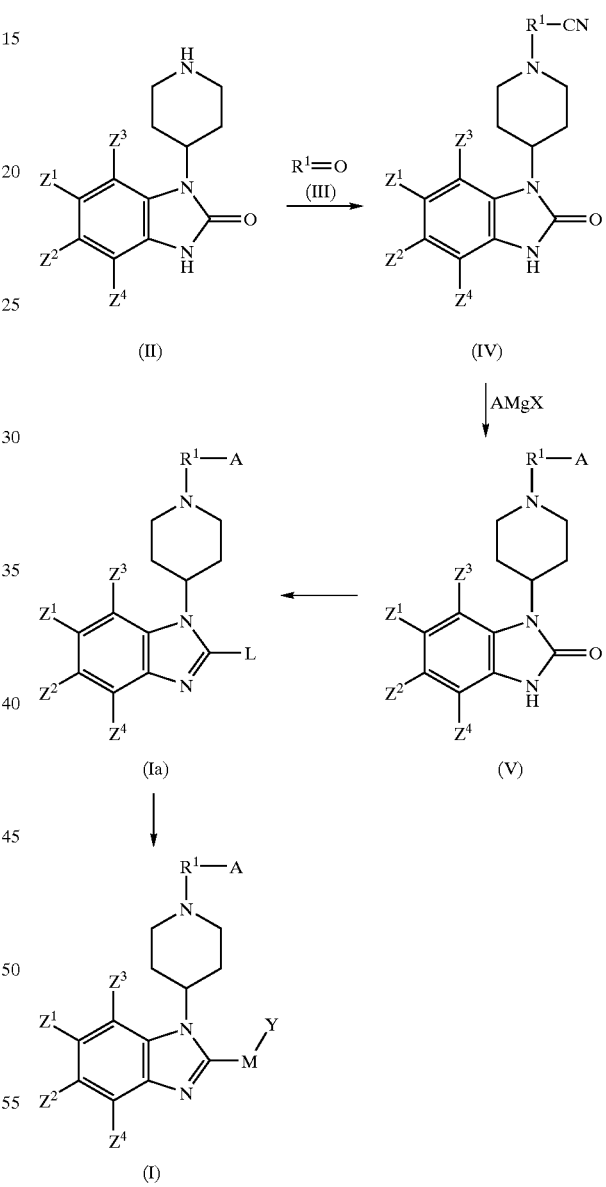

As shown in Scheme 1, a compound of formula (Ia), wherein L represents a leaving group such as halo, may be obtained from a 2-oxo-benzimidazolyl compound of formula (II) via intermediate compounds of formulae (IV) and (V).

According to Scheme 1, first, a compound of formula (II) may be subjected to the Strecker synthesis with the stoichiometric amount of a cyclic ketone compound of formula (III)

to give the compound of formula (IV). Second, the resulting compound of formula (IV) may be reacted with a Grignard reagent of formula AMgX (wherein X is halo) to give the compound of formula (V). Then, the compound of formula (V) may be reacted with a suitable nucleophilic reagent to yield the compound of formula (Ia). The Strecker synthesis may be carried out using a suitable cyanating agent according to known procedures reported in A. Kalir, et al., *J. Med. Chem.* Vol. 12, p. 473, 1969. Suitable cyanating agents include cyanide such as potassium cyanide (KCN). This reaction may be carried out at pH in the range of about 3 to 11 at about 0° C. (e.g., in ice-cool water).

The reaction of the compound of formula (IV) with a Grignard reagent may be carried out under anhydrous condition according to known procedures (e.g., O. A. Al-Deeb, *Arzneim.-Forsch./Drug Res.*, Vol. 44 (11), Nr. 10, 1994). More specifically, this reaction may be carried out in a suitable solvent such as tetrahydrofuran (THF) or ether, at from −78° C. to the reflux temperature of the reaction mixture for from about 30 minutes to about 48 hours. Preferably, the Grignard reagent may be added to the reaction mixture at about 0° C., and then the reaction mixture may be allowed to warm to room temperature for further reaction.

The compound of formula (V) thus obtained may be refluxed with a suitable nucleophilic reagent to give the compound of formula (Ia). Suitable nucleophilic reagents used in this reaction include compounds represented by formula $POL_3$ such as phosphoryl trichloride. This reaction may be carried out under conditions for example reported in R. Iemura et al., *J. Med. Chem.* Vol. 29, pp. 1178–1183, 1986.

To the compound of formula (Ia) thus obtained, may be subjected to a reaction with a compound represented by Y-M-H under known reaction conditions to afford the compound of formula (I). This reaction may be carried out in a reaction inert solvent at from about 0° to about 200° C. (preferably from 100° to 150° C.) for from about 1 hour to about 7 days (preferably from about 10 hours to about 5 days). Suitable reaction inert solvents include alkanols such as methanol, ethanol, isopropyl alcohol and tert-butyl alcohol, and N,N-dimethylformamide (DMF) and the like. If appropriate, this reaction may be carried out in a suitable reaction chamber such as an autoclave or a sealed tube. A reaction of a compound of formula (Ia) wherein L is Cl with an imide compound represented by Y-M-H may be carried out according to the procedures reported by C. H. Senanayake, et al., *Tetrahedron Lett.*, Vol. 38, pp. 5607–5610, 1997. In the report, Pd-catalyst is used in the presence of a base in toluene with heating. Compounds represented by Y-M-H or an amino protected compounds thereof employed in the reactions of compounds of formula (Ia) illustrated in Scheme 1 may be prepared according to known procedures (e.g. D. Barlocco et al., *J. Med Chem.*, Vol. 41, pp. 674, 1998, K. P. B. ges et al., *J. Med Chem.*, Vol. 38, pp. 4380, 1995 S Oida et al., JP7101959, T. Schenke et al., EP393424, K. E. Brighty et al., *Synlett*, Vol 11, pp. 1097, 1996 and de Costa B. R. et al, *J. Med Chem.*, Vol. 36, pp. 2311, 1993). A compound of formula (I) wherein M is oxygen may be prepared by a coupling reaction of a compound of formula (Ia) with an appropriate hydroxy substituted azaheterocyclic compound in the presence of a base in a reactio inert solvent. For example, tropine may be coupled with a compound of formula (Ia) in the presence of NaH in DMF. A compound of formula (I) wherein M is nitrogen may be prepared by condensing a compound of formula (Ia) with an appropriate amine compound in a reaction inert solvent if required at an elevated temperature.

In addition, a compound of formula (I) wherein M is S may be prepared according to known preparation methods described, for example, in WO 00/08013. The sulfide compounds may further be oxidized to the corresponding sulfonyl compound under conventional oxidation-conditions with thioethers using an oxidizing reagent such as potassium permanganate.

A compound of formula (I) wherein M is NH and Y is an amino substituted group, may be subjected to a further cyclization to give a compound of formula (I) wherein M is a covalent bond and Y is a bicyclic ring. The cyclization may be carried out by carbonylation known to those skilled in the art. Typically, this carbonylaton may be carried out using triphosgene in a reaction inert solvent such as benzene.

A compound of formula (II) employed in Scheme 1 may be prepared by carbonylation of a diamine compound of formula (X).

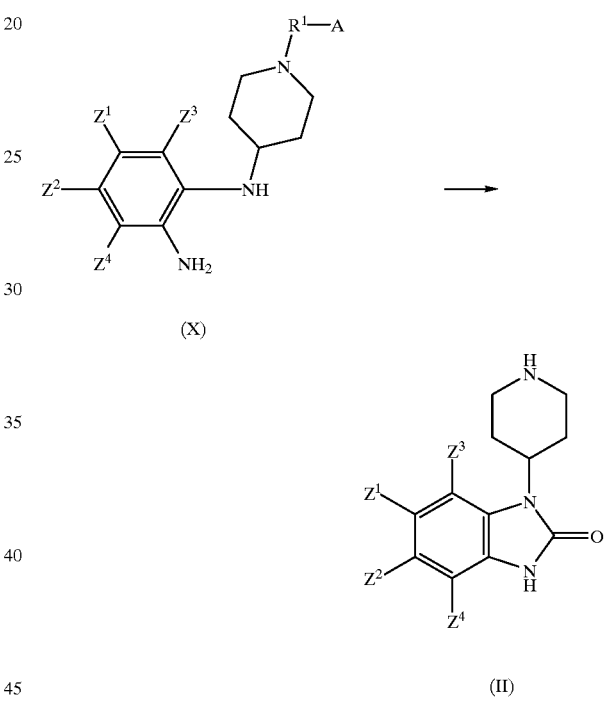

The carbonylation may be carried out by reacting a compound of formula (X) with a suitable carbonylating agent such as carbonyldiimidazole, trichloromethyl chloroformate, triphosgene or urea. This reaction may be carried out in a reaction inert solvent such as THF, benzene, toluene or chloroform, at the temperature in the range of from about 0° to about 120° C., for from about 0.5 to about 24 hours. The reaction may be conducted according to the procedures described in WO 98/54168.

Nucleophiles to be reacted with a compound of formula (Ia) in the reaction in Scheme 1 may be known compounds or prepared from a known compound using procedures known to those skilled in the art. Examples of the preparation procedures include subjecting (a) 3,4-pyridinedicarboximide to hydrogenation and reduction to give a octahydro-1H-pyrro[3,4-c]pyridine compound; and (b) an imine compound to a reaction with a N-protected amino acid or its derivatives in the presence or absence of an aldehyde compound, and an optional subsequent reduction to give an azahetero cyclic nucreophile.

The reaction procedures are described in *J. Med. Chem.* 1993, 36, 2311 by de Costa B. R. et al.; European Patent Publication No. 603,887; and Bull. Soc. Chim. Fr. 579–83, 1988 by M. Jouclaa et al. Through the preparation of the nucleophiles, amino or imino moieties of the reactants or intermediate compounds may be protected with appropriate N-protecting groups, and the N-protecting groups may be removed at an appropriate reaction step. Alternatively, the N-protecting group may be removed after the nucleophilic reaction with a compound of formula (Ia).

Scheme 2 illustrates other preparation methods for compounds of formula (I). Following the preparation methods in this reaction scheme, compounds of formula (Ib) may also be prepared. Compounds of formula (Ib) may be subjected to further reactions as reaction intermediate compounds to give compounds of formula (I).

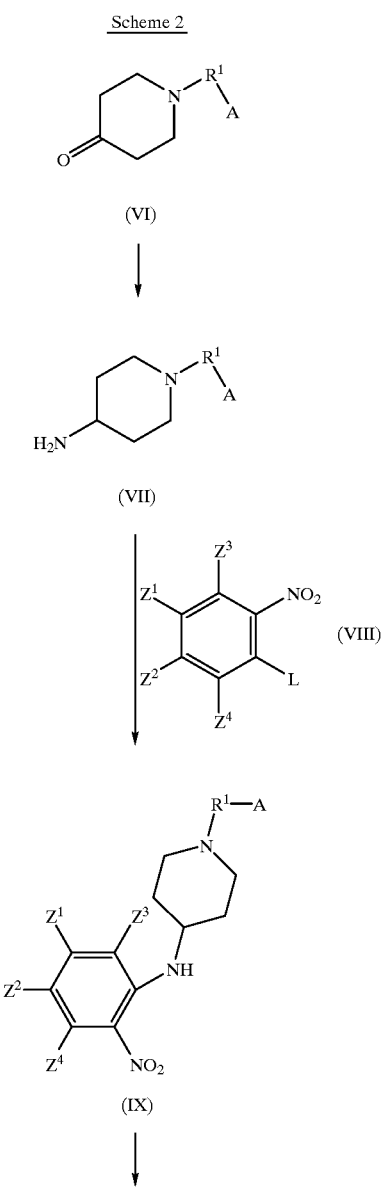

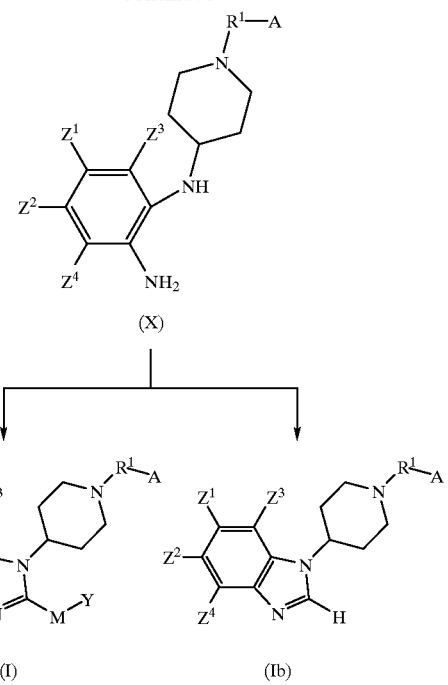

As shown in Scheme 2, compounds of formula (I) or (Ib) may be prepared through the process comprising the following reaction steps:

(a) reductive amination of a piperidine-4-one compound of formula (VI) to give the 4-aminopiperidine compound of formula (VII);

(b) coupling reaction of the compound of formula (VII) with a nitrobenzene compound of formula (VIII) wherein L is a leaving group, such as halo, to give the nitroaniline compound of formula (IX);

(c) reduction of the resulting nitroaniline compound of formula (IX) to give the diamine compound of formula (X); and (d) benzimidazole ring formation with the compound of formula (X) to give the compound of formula (I) or (Ib)

Each reaction step is more specifically described as follows:

(a) The reductive amination may be conducted by an oximation of the piperidine 4-one compound of formula (VI) followed by reduction. Both of the reactions may be conducted under conditions for oximation of carbonyl compounds known to those skilled in the art. For example, the oximation may be carried out by a reaction of the piperidine compound with hydroxylamine in the presence or absence of a base, such as $K_2CO_3$, in a reaction inert solvent such as alcohol at about room temperature for about 0.5 to 48 hours. The resulting oxime compound may be extracted and subjected to reduction under known conditions to give the amine compound of formula (VII). The reduction may be carried out in the presence of a reducing reagent, such as lithium aluminum hydride, in a reaction inert solvent, such as THF, at about 0° C. to room temperature for from about 0.5 to 48 hours. These reactions are described in B. de Costa et al., *J. Chem. Soc. Perkin. Trans.*, Vol. 1, pp. 1671–1680, 1992.

(b)–(c) Steps (b) and (c) may be carried out under conditions known to those skilled in the art (e.g., N. A. Meanwell et al., *Bioorganic & Medicinal Chemistry Letters*, Vol. 6, No. 14, pp. 1641–1646, 1996). For example, coupling reaction (b) may be carried out in the presence of a base, such as $K_2CO_3$ and triethylamine ($NEt_3$), in a reaction inert solvent, such as acetonitrile, under reflux for about 0.5 to 48 hours. Then, the resulting compound of formula (IX) may be extracted and subjected to reduction to give the compound of formula (X). The reduction may be carried out in the presence of a suitable reducing reagent, such as Sn, Zn or Fe and acid, in a reaction inert solvent, such as ethanol, at a temperature in the range from room temperature to the reflux temperature of the reaction mixture (preferably under reflux) for from about 0.5 to about 48 hours. The reduction may also be carried out under known hydrogenation conditions such as in the presence of a metal catalyst such as Raney nickel catalyst, palladium catalyst and platinum catalyst at a temperature in the range from about 0° to 100° C. (preferably at about room temperature) under hydrogen atmosphere in a reaction inert solvent such as methanol, ethanol or THF in the presence or absence of hydrogen chloride for from about 0.5 hours to 2 days.

(d) A compound of formula (X) may be cyclized to form a benzimidazole ring by reaction with an appropriate cyclizing reagent to give the compound (I) or (Ib) in a reaction inert solvent in the presence or absence of a coupling reagent. Suitable cyclizing reagents include a carboxylic acid, an amino carboxylic acid, an acid anhydride (e.g., acetic anhydride, isobutyric anhydride, benzoic anhydride, isonicotinic anhydride and the like) a formamidine (e.g., formamidine alkylate such as formamidine acetate), an alkyl carbonyl halide (e.g., a cycloalkyl carbonyl halide, bicyclic or bicyclic-heterocyclic-carbonyl halide, spirocarbocyclic- or spiro-heterocyclic-carbonyl halide), an aryl or an aryl alkyl carbonyl halide (e.g., phenylacethyl halide), an heteroaryl carboxylic acid (e.g., a piperidinyl carboxylic acid compound), carbon disulfide, cyanogen halide (e.g., cyanogen bromide), cyanamide, trialkyl orthoformate (e.g., triethyl orthoformate), and the like. Suitable solvents are tetrahydrofuran (THF), xylene, ethoxyethanol and the like. Suitable coupling reagents are those typically used in peptide synthesis including dicyclohexylcarbodiimide (DCC), diisopropylcarbodiimide (DIPC), 1-ethyl-3-(3-dimethylaminopropyl) carbodiimide (WSC), benzotriazole-1-yloxy-tris (dimethylamino)phosphonium hexafluorophosphate (BOP), diphenylphosphorylazide (DPPA) and the like. This reaction may be carried out at from about 0° C. to the reflux temperature of the reaction mixture, preferably from about room temperature to the reflux temperature for about 1 minute to about 120 hours, preferably for from about 10 minutes to about 72 hours. An embodiment of the 2-aminobenzimidazole ring formation is also reported in N. A. Meanwell et al., *Bioorganic & Medicinal Chemistry Letters*, Vol. 6, No. 14, pp. 1641–1646, 1996. These reactions are also reported in A. F. Pozharskii et al., Russ. Chem. Rev. (English Translation), Vol. 35. P. 122-, 1996.

Alternatively, a compound of formula (X) may be subjected to a coupling reaction with an isothiocyanate compound and a subsequent desulfurization under known conditions to give a compound of formula (I) wherein M is NH. For example, the first coupling reaction may be carried out in a reaction inert solvent such as an alkanol (e.g., ethanol) at from about room temperature to 100° C. from 30 minutes to 48 hours under stirring. The desulfurization may be carried out in the presence of an alkyl halide under reflux for from about 30 minutes to 48 hours.

A compound of formula (Ib) thus obtained may be converted to a compound of formula (I) wherein M is carbonyl (C=O). This reaction may be carried out according to reaction methods known to those skilled in the art. For example, a compound of formula (Ib) may be reacted with a lithiation reagent such as n-BuLi under known conditions followed by reaction with an appropriate amide compound such as an N,N-alkylalkoxy amide under known conditions. The former reaction may be carried out at about −78° C. in a reaction inert solvent such as THF for from about 30 minutes to 48 hours. The latter reaction may be carried out according to known procedures reported by G. Bitan et al., *J. Chem. Soc., Perkin. Trans.* Vol. 1, pp. 1501–1510, 1997. Typically, this reaction may be conducted at about −78° C. to ambient temperature in THF for about 30 minutes to 24 hours.

A compound of formula (Ib) may be also converted into a compound of formula (I) through an ester group introduction and reduction of the ester group. The ester group may be introduced to a compound of formula (Ib) by a metallation using butyllithium in the presence of hexamethylphosphoramide (HMPA) and a subsequent reduction using a reducing agent such as $LiAlH_4$. The aldehyde compound thus obtained may be coupled with a desired amine or imine compound to give a compound of formula (I). The coupling reaction may be carried out in the presence of a reducing agent such as sodium triacetoxyborohydride and acetic acid.

Further, compounds of formula (I) wherein Y has an amino or imino group at its terminal position, or a protected amino or imino group, may be subjected to a further modification described as follows:

(i) Modification 1—Acylation of the compound of formula (I):

Those compounds of formula (I) may be reacted with an alkylcarbonyl halide at about room temperature in a basic solvent to give an amide compound. The amine or imine compounds may be reacted with an amino acid, or an amino acid sulfone or sulfoxide in the presence or absence of a coupling reagent known to those skilled in the art in peptide synthesis. Suitable coupling reagents include WSC and the like.

(ii) Modification 2—Coupling of the compound of formula (I) with an amino acid:

Those compounds of formula (I) may be coupled with an amino acid, an amino acid sulfone or sulfoxide, or a phthalimido alkyl sulfonyl halide under conventional amide formation conditions in the presence of a coupling reagent in a reaction inert solvent such as acetonitrile at about room temperature. These amino acids include isoleucine, alanine, methionine, proline, phenylalanine, valine, and the like. Suitable coupling reagents are those typically used in peptide synthesis including WSC, dicyclohexylcarbodiimide (DCC), N,N'-carbonyldiimidazole (CDI), $POCl_3$, $TiCl_4$, $SO_2ClF$, benzotriazol-1-yl diethyl phosphate, $Ti(Obu)_4$, molecular sieves, N,N,N',N'-tetramethyl (succinimido)uronium tetrafluoroborate, CBMIT, Lawesson's reagent, chlorosulfonyl isocyanate, $P_2I_4$, pyridinium salts-$Bu_3N$, and a mixture of $Bu_3P$ and PhCNO.

(iii) Modification 3—Guanidylation of the compound of formula (I):

Those compounds of formula (I) may be also reacted with a guanidine compound under known conditions. A suitable reaction condition comprises reaction with an amino-protected guanidine compound in a reaction inert solvent such as THF at about room temperature (see M. S. Bematowicz, et al., *Tetrahedron Lett.*, Vol. 34, p. 3389–3392,1993).

(iv) Modification 4—Reductive amination:

Those compounds of formula (I) may be also subjected to a reductive amination to give terminal N-alkylated compound. The reductive amination of those compounds of formula (I) can be carried out under known conditions. For example, this reductive amination can be carried out in the presence of a reducing agent such as sodium cyanoborohydride ($NaBH_3CN$) and carbonyl compound such as formalin, in the presence or absence of acetic acid in a suitable solvent such as acetonitrile at about room temperature for about 1 hour to 2 hours.

(v) Modification 5—Reduction of the protected amino or protected imino group:

Those compounds of formula (I) may be converted to the alkyl group by reduction. The reduction by suitable reducing agent such as lithium aluminum hydride may be carried out in a reaction inert solvent such as tetrahydrofuran at from about 0° C. to about reflux temperature for about 1 day.

Modification 5—Alkylsulfoanmide or Urea Formation:

Compounds of formula (I) wherein Y has an amino group may be converted to an alkyl sulfonamide or urea compound under conditions known to those skilled in the art. The alkyl sulfonamide compound of formula (I) may be prepared using mesyl chloride in the presence of triethylamine. The urea compounds of formula (I) may be prepared using 1,1'-carbonyldiimidazole in a reaction inert solvent such as THF, and the urea compound of formula (I) may be isolated by basification with a base such as $NH_4OH$ to the reaction solution.

Intermediate compounds (VI) may be prepared by the methods illustrated in

Scheme 3

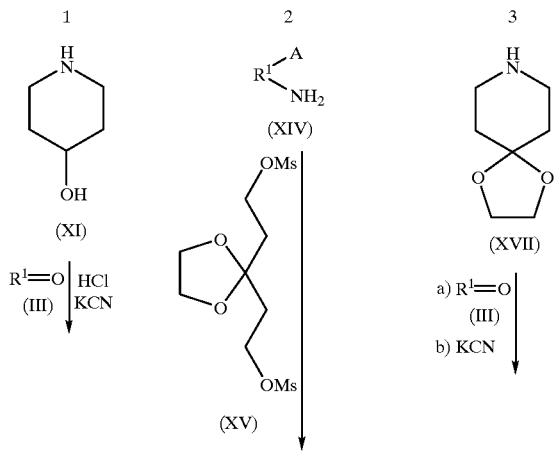

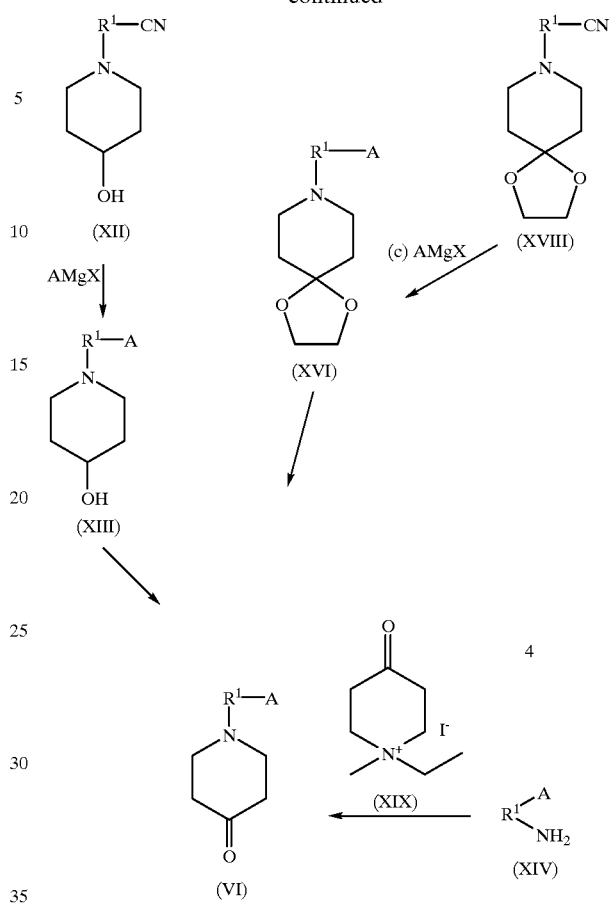

Route 1:

This reaction route illustrates preparation procedures to give a compound of formula (VI) from 4-piperidinol of formula (XI) according to the procedures reported in A. Kalir et al., *J. Med. Chem.*, Vol. 12, pp. 473–477, May 1996. First, a compound of formula (XI) may be condensed with a compound of formula (III) and cyanated to give the compound of formula (XII). Second, the obtained compound of formula (XII) may be reacted with a Grignard reagent AMgX wherein X is halo to give the compound of formula (XIII). Then, resulting compound of formula (XIII) may be oxidized to give the compound of formula (VI). The condensation and cyanation may be carried out using 4-piperidinol HCl salt in water at about room temperature.

Route 2:

This reaction route illustrates a preparation procedure for a compound of formula (VI) from a starting amine (XIV) comprising condensation of a compound of formula (XIV) with 3,3-ethylenedioxypentane-1,5-diol dimethanesulfonate (XV) followed by deprotection. These reactions may be carried out under known conditions (e.g., B. de Costa et al., *J. Chem. Soc. Perkin. Trans.*, Vol. 1, p. 1671, 1992 and R. L. McQuinn et al., *J. Med. Chem.* Vol. 24, pp. 1429–1432, 1981).

Route 3:

This reaction route illustrates a preparation procedure for a compound of formula (VI) from a known 4-piperidone ethylene ketal (XVII). This preparation comprises (a) condensation of a compound of formula (XVII) with a ketone compound of formula (III), (b) cyanation, (c) reaction of the compound of formula (XVIII) with a Grignard reagent and (d) deprotection of the compound of formula (XVI). These reactions may be carried out under the similar conditions to those described in Scheme 1.

Route 4:

This reaction route illustrates a preparation procedure for a compound of formula (VI) from a starting amine (XIV) comprising condensation of a compound of formula (XIV) with iodide salt of N-methyl-N-ethylpiperidone (XIX) This reaction may be carried out under known conditions (e.g., D. M. Tschaen et al, *J. Org. Chem.*, Vol.60, p. 4324, 1995).

The starting amine compounds of formula (XIV) used in the above reaction scheme may be readily prepared by methods known for those skilled in the art (e.g., J. Weinstock, et al., OS IV 910, E. J. Cone, et al., *J. Med. Chem.*, Vol. 24, pp. 1429–1432, 1981, M. Goodman et al.,*J. Med. Chem.*, Vol. 27, pp. 1663, 1984,and Ritter Reaction described in *Org. React.* Vol. 17, pp. 313–325, 1969). Compounds of formula (XI) and (XVII) are commercially available or may readily be prepared methods known by those skilled in the art.

In addition, compounds of formula (I) wherein A is hydroxy($C_1$–$C_4$)alkyl may be prepared by reduction of compounds of formula (I) wherein A is ($C_1$–$C_4$)alkoxy-(C=O). The reduction by suitable reducing agent such as lithium alminum hydride may be carried out in a reaction inert solvent such as tetrahydrofuran at from about 0° C. to about room temperature for about 2 to 3 hours.

The starting materials (III), (XVII), (XIX) and the other reactants used in the reactions described above are known or commercially available compounds, or may be prepared according to known procedures for a person skilled in the art.

In the each reaction described above, unless indicated otherwise, the reaction pressure is not critical. Generally, the reactions will be conducted at a pressure of about one to about three atmospheres, preferably at ambient pressure (about one atmosphere).

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, 35S, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deutrium, i.e., $^2H$, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, by submitting a readily available isotopically labelled reagent for a non-isotopically labelld reagent.

The compounds of Formula (I) of this invention are basic, therefore they will form acid-addition salts. All such salts are within the scope of this invention. However, it is necessary to use an acid addition salt which is pharmaceutically-acceptable for administration to a mammal. The acid-addition salts can be prepared by standard methods. For example, the salts may be prepared by contacting the basic compounds with acid in substantially equivalent proportions in water or an organic solvent such as methanol or ethanol, or a mixture thereof. The salts can be isolated by crystallization from or evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, ethanesulfonate, benzenesulfonate, p-toluenesulfonate, oxalate and pamoate (1,1'-methylene-bis-(2-hydroxy-3-naphtoate)) salts.

The compounds of formula (I) of this invention may contain one or more asymmetric centers and thus may exist as diastereomers. The invention includes both distereomeric mixtures as well as the separated individual diastereomers.

In addition, when the compounds of this invention form hydrates or solvates they are also within the scope of this invention.

The compounds of Formula (I) have been found to possess selective affinity for ORL1-receptors and ORL-1 receptor agonist activity. Thus, these compounds are useful as an analgesic, anti-inflammatory, diuretic, anesthetic, neuroprotective, anti-hypertensive and anti-anxiety agent, and the like, in mammalian subjects, especially humans in need of such agents. The affinity, agonist activities and analgesic activity can be demonstrated by the following tests respectively.

Selective Affinity for ORL1-receptors:

The following affinity assays were carried out using methods well known in the art.

ORL1-receptor Affinity:

The ORL1 receptor binding affinity of the compounds of this invention were determined by the following procedures. Human ORL1 receptor transfected HEK-293 cell membranes (purchased from Receptor Biology Inc.) and wheat-germ agglutinin coated SPA beads (purchased from Amersham) were combined with 0.4 nM[$^3H$]nociceptin and unlabeled test compounds in 200$\mu$l of 50 mM Hepes buffer pH7.4 containing 10 mM $MgCl_2$ and 1 mM EDTA. This mixture was incubated at room temperature (abbreviated as rt) for 30 min to 60 min. Non specific binding was determined by the addition of 1 $\mu$M nociceptin. Radioactivity was counted by Wallac 1450 MicroBeta Liquid Scintilation Counter.

$\mu$-receptor Affinity:

The mu ($\mu$) opioid receptor binding affinity of the compounds of this invention were determined by the following procedures. Human-mu opioid receptor transfected CHO-K1 cell membranes (purchased from Receptor Biology Inc.) and wheat-germ agglutinin coated SPA beads were combined with 1.0 nM[$^3H$]DAMGO and unlabeled test compounds in 200 $\mu$l of 50 mM Hepes buffer pH7.4 containing 10 mM $MgCl_2$ and 1 mM EDTA. This mixture was incubated at rt for 30 minutes to 60 minutes. Non specific binding was determined by the addition of 1 $\mu$M DAMGO. Radioactivity was counted by Wallac 1450 MicroBeta.

κK-receptor Affinity:

The kappa (κ) opioid receptor binding affinity of the compounds of this invention were determined by the following procedures. Human kappa-opioid receptor transfected CHO-K1 cell membranes (purchased from Receptor Biology Inc.) and wheat-germ agglutinin coated SPA beads were combined with 0.5 nM[$^3$H]CI-977 and unlabeled test compounds in 200 $\mu$l of 50 mM Hepes buffer pH7.4 containing 10 mM MgCl$_2$ and 1 mM EDTA. This mixture was incubated at rt for 30 minutes to 60 minutes. Non specific binding was determined by the addition of 1 $\mu$M CI-977. Radio activity was counted by Wallac 1450 MicroBeta.

δ-receptor Affinity:

The delta (δ) opioid receptor binding affinity of the compounds of this invention were determined by the following procedures. Human delta opioid receptor transfected CHO-K1 cell membranes (purchased from Receptor Biology Inc.) and wheat-germ agglutinin coated SPA beads were combined with 2.0 nM[$^3$H]DPDPE and unlabeled test compounds in 200 $\mu$l of 50 mM HEPES buffer pH7.4 containing 10 nM MgCl$_2$ and 1 mM EDTA. The assay was incubated at room temperature for 30 minutes to 60 minutes. Non specific binding was determined by the addition of 1 $\mu$M of each non-labeled ligand. Radioactivity was counted by Wallac 1450 MicroBeta.

Each percent non specific binding thus obtained was graphed as a function of compound concentration. A sigmoidal curve was used to determine 50% bindings (i.e., IC$_{50}$ values). This calculation was made using methods well known in the art.

In this testing, all the compounds prepared in the working examples appearing hereafter demonstrated higher affinity on ORL1-receptors than on mu-receptors as defined by the following equation.

$$IC_{50} \text{ (ORL1-receptors) nM/IC}_{50} \text{ (mu-receptors) nM} < 1.0$$

Functional Assay:

The functional activity of the compounds of this invention in each opioid receptor was determined in 35S-GTPγS binding system according to the procedures reported by L. J. Sim, R. Xiao and S. Childers *Neuroreort* Vol. 7, pp. 729–733, 1996. Human ORL1-, mu-, kappa- and delta-receptor transfected CHO-K1 or HEK cell membranes were used. The membranes were suspended in ice-cold 20 mM HEPES buffer pH 7.4, containing 100 mM NaCl, 10 mM MgCl$_2$ and 1 mM EDTA. 0.17 mg/ml of Dithiothreitol (DTT) was added to this buffer prior to use. Membranes were incubated at 25° C. for 30 minutes with the appropriate concentration of test compounds in the presence of 5 $\mu$M GDP, 0.4 nM of 35S-GTPγS and Wheat-germ agglutinin (WGA) coated SPA bead (1.5 mg) in a 0.2 ml total volume. Basal binding was assessed in the absence of agonist, and non-specific binding is determined with 10 $\mu$M GTPγS. Radio activity was counted by Wallac 1450 MicroBeta. Most of the compounds of this invention prepared in the following working examples exhibited good ORL1agonists activity in this assay.

Analgesic Tests

Tail Flick Test

Male ICR mice, 4 weeks old and weighing 19–25 g, are used. The training sessions are performed until mice can flick their tails within 4.0 sec by using Analgesia Meter MK-330A (Muromachi Kikai, Japan). Selected mice are used in this experiment. The latency time is recorded twice at 0.5, 1.0, and 2.0 hours after administration of the compound. The intensity of the beam is set to 80. Cut-off time is set to 8.0 second. A compound of this invention is subcutaneously administered 30 minutes before the test. The ED$_{50}$ value is defined as the dose of a compound tested which reduces by half the frequency of the tail flicking observed in a control group.

Acetic Acid Writhing Test

Male ICR mice, 4 weeks old and weighing 21–26 g, are placed on a fast the day before use. A compound of the invention is dissolved in 0.1% methyl cellulose(MC)-saline and subcutaneously administered to the mice 0.5 hours after the compund injected. Acetic acid is diluted with saline to the concentration of 0.7%(v/v) and is injected intraperitoneally (0.2 ml/10 g of body weight) into the mice with a 26 gauge needle. After the acetic acid injection, each animal is placed in a 1 L beaker and recorded by a video tape recorder. The frequency of writhing is counted from 5 to 15 min after the acetic acid injection. The ED$_{50}$ value, defined as the dose of the compounds tested which halves the writhing is observed in the control group.

Formalin Licking Test

Male SD rats (80–100 g) are injected subcutaneously with a test compound dissolved in 0.1% methyl cellulose (MC)-saline or vehicle. After 30 minutes, 50 $\mu$l of a 2% formalin are injected into a hind paw. The number of licking the injected paw per observation period is measured from 15 to 30 minnutes after the injection of formalin and expressed as % inhibition compared to the respective vehicle group. This testing method is known to those skilled in the art and described in, for example, (1) R. L. Follenfant, et.al., Br. J. Pharmacol. 93, 85–92 (1988); (2) H. Rogers, et.al., Br. J. Pharmacol. 106, 783–789 (1992); and (3) H. Wheeler-Aceto, et al., Psychopharmacology, 104, 35–44 (1991).

Carrageenan-induced Mechanical Hyperalgesia in Rats

A compound to be tested is dissolved in 10% Sulfobutyl Ether Cyclodextrin (SBECD) containing saline. Trained male rats, 4 week old, is purchased from Japan SLC (Shizuoka, Japan) and is habituated to testing for 2 days. The response to mechanical nociceptive stimulus is assessed using Ugo Basile algesiometer (Milan, Italy). Mechanical pressure is applied to rats right hind paw gradually, with a loading rate of 16 g/second, until a withdrawal response occurred. The withdrawal behavior is considered as nociceptive response. The pressure that elicited the paw-withdrawal response is measured. Acute inflammation is produced by intraplanter (i. pl.) injection with a 1% lambda-carrageenan into the planter skin of rats right hind paw (0.1 ml/paw). The nociceptive response is redetermined at 3.5 and 4.5 h after the carrageenan-injection, when inflammation is prominent. Paw pressure scores for compound-treated rats are expressed as a percentage inhibition of the hyperalgesia induced by carrageenan. Compounds are administered subcutaneously (s.c.) to rats 0.5 hour before the measurement. The number of animals per group is eight. In each test, morphine (3 mg/kg, s.c.) is used as a positive control. Statistical analysis of experimental data is calculated by using one-way analysis variance test (ANOVA) or t-test and p<0.05 is considered as statistically significant.

References

1) Boyce S., Wyatt A., Webb J. K., O'Donnell R., Mason G., Rigby M., Sirinathsinghji D., Hill R. G., Rupniak N. M. J., 1999. Selective NMDA NR2B antagonists induce antinociception without motor dysfunction: correlation with restricted localization of NR2B subunit in dorsal horn. Neuropharmacology 38, 611–623.

2) Boyce S., Chan, C.-C., Gordon, R., Li, C.-S., Rodger, I. W., Webb, J. K. Rupniak. N. M. J., Hill R. G., 1994. L-745,337: a selective inhibitor of cyclogenase-2 elicits antinociception but not gastric ulceration in rats. Neuropharmacology 33, 1609–1611.

CCI (Chronic Constriction Injury) Model

SD rats (9 weeks, Nippon SLC) were used. Chronic constriction surgery (left side) was made according to Bennett's method (Eliav E., Herzberg U., Ruda M A. & Bennett G J., Pain, 83 (2): 169–182, 1999). The allodynic effect was induced one week after surgery and reached a plateau two weeks later.

Fifteen days after surgery, a compound to be tested was subcutaneously or orally administered to chronic construction injury (abbreviated as CCI) rats. An analgesic test (von Frey Hair test) was performed at 0.5 and 2 hours after drug administration. The number of animals per group was eight. Statistical analysis of experimental data was calculated by using one-way analysis variance test (ANOVA) or t-test and p<0.05 was considered as statistically significant. A preferred compound of this invention having good selectivity on ORL1-receptor exhibited a low $ED_{50}$ value in subcutaneous administration.

The compounds of Formula (I) of this invention can be administered by conventional pharmaceutical practice via either the oral, parenteral or topical routes to mammals, for the treatment of the indicated diseases. For administration to a human patient by any of those routes, the dosage is in the range of about 0.01 mg/kg to about 3000 mg/kg body weight of the patient per day, preferably about 0.01 mg/kg to about 1000 mg/kg body weight per day administered singly or as a divided dose. However, variations will necessarily occur depending upon the weight and condition of the subject being treated, the compound employed, the disease state being treated and the particular route of administration chosen.

The compounds of the present invention may be administered alone or in combination with pharmaceutically acceptable carriers by either of the above routes previously indicated, and such administration can be carried out in single or multiple doses. Generally, the compounds can be combined with various pharmaceutically acceptable carriers in the form of tablets, powders, capsules, lozenges, trochees, hard candies, powders, sprays, creams, salves, suppositories, jellies, gels, pastes, lotions, ointments, suspensions, solutions, elixirs, syrups or the like. Such pharmaceutical carriers include solvents, excipients, coating agents, bases, binders, lubricants, disintegrants, solubilizing agents, suspending agents, emulsifing agents, stabilizers, buffering agents, tonicity agents, preservatives, flavorating agents, aromatics, coloring agents and the like.

For example, the tablets can contain various excipients, such as starch, lactose, glucose, microcrystalline cellulose, calcium sulfate, calcium carbonate, talc, titanium oxide and the like; coating agents, such as gelatin, hydroxypropylcellulose and the like; binding agents, such as gelatin, gum arabic, methylcellulose and the like, and the disintegrating agents such as starch, agar, gelatine, sodium hydrogencarbonate and the like. Additionally, lubricating agents, such as magnesium stearate and talc, are often very useful for tabletting purposes. Solid compositions of a similar type may also be employed as fillers in gelatine capsules; preferred materials in this connection also include lactose, as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin and various like combinations thereof.

In general, the therapeutically-effective compounds of this invention are present in such oral dosage forms at concentration levels ranging 5% to 70% by weight, preferably 10% to 50% by weight.

The compounds of the present invention in the form of a solution may be injected parenterlly such as intradermaly, subcutaneously, intravenously or intramuscularly. For example the solutions are sterile aqueous solutions, aqueous suspensions and an edible oil solutions. The aqueous solutions may be suitably buffered (preferably pH>8), and may contain enough salts or glucose to make the solution isotonic with blood. The aqueous solutions are suitable for intravenous injection purposes. The aqueous suspensions may contain a suitable dispersing or suspending agents such as sodium carboxymethylcellulose, methylcellulose, polyvinylpyrrolidone or gelatin. The aqueous suspensions can be used for subcutaneous or intramuscular injections. Edible oils such as cottonseed oil, sesame oil, coconut oil or peanut oil, can be employed for the edible oil solutions. The oil solutions are suitable for intra-articular, intramuscular and subcutaneous injection. The preparation of all these solutions under sterile conditions is readily accomplished by standard pharmaceutical techniques well-known to those skilled in the art.

It is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparation. However, it should be understood that the invention is not limited to the specific details of these examples and preparations. Melting points were taken with a Büchi micro melting point apparatus and is not corrected. Infrared Ray absorption spectra (IR) were measured by a Shimadzu infrared spectrometer (IR-470). $^1$H and $^{13}$C nuclear magnetic resonance spectra (NMR) were measured in $CDCl_3$ by a JEOL NMR spectrometer (JNM-GX270, 270 MHz. Uunless otherwise indicated, peak positions are expressed in parts per million (ppm) downfield from tetramethylsilane, are denoted as follows: s, singlet; d, doublet; t, triplet; m, multiplet; br, broad. In the working examples and preparations, MeOH means methanol; $Et_2O$ means diethyl ether; THF means tetrahydrofuran; DMF means N,N-dimethylformamide; and HMPA means hexamethylphosphoramide.

Preparation 1

2-Chloro-1-[1-(1-phenylcycloheptyl)-4-piperidinyl]-1H-benzimidazole

A mixture of 4-(2-keto-1-benzimidazolinyl)piperidine (5.10 g, 23.5 mmol) and 10% HCl solution in MeOH (20 ml) was stirred at room temperature for 10 minutes. After evaporation of the solvent, the residue was triturated in $Et_2O$ to give HCl salt of 4-(2-keto-1-benzimidazolinyl)piperidine as off-white powder. To this HCl salt of 4-(2-keto-1-benzimidazolinyl)piperidine was added cycloheptanone (3.33 ml, 28.2 mmol) followed by addition of aqueous solution of KCN (1.92 g, 29.5 mmol) in water (7 ml) at room temperature. After 18 hours stirring, the resulting solid was collected by filtration, washed with water, and dried in vacuo to give 6.81 g (85.7%) of the nitrile derivative thus obtained as white powder. To a solution of this nitrile derivative (5.12 g, 15.1 mmol) in THF (40 ml) was added a solution of phenylmagnesium bromide in $Et_2O$ (3.0 M solution, 25 ml) at 0° C. Then the reaction mixture was stirred at room temperature for 18 hours. Aqueous $NH_4Cl$ solution was added to the reaction mixture and the resulting solid appeared was collected by filtration, washed with water and Et₂O, and dried in vacuo at 70° C. to give 4.88 g (82.8%) of 1-[1-(1-phenylcycloheptyl)-4-piperidinyl]-1,3-dihydro-2H-1,3-benzimidazol-2-one as white powder. A mixture of 1-[1-(1-phenylcycloheptyl)-4-piperidinyl]-1,3-dihydro-2H-1,3-benzimidazol-2-one (2.316 g, 5.95 mmol) and phosphoryl chloride (15 ml, 165.5 mmol) was heated to reflux for 1.5 hours. After cooling down to room temperature, the reaction mixture was poured into ice cooled 25% ammonia solution and extracted with CH₂Cl₂. The extracts combined were washed with brine, dried (Na₂SO₄), filtered, and concentrated. The residue was purified by column chromatography (silica gel: 200 g, hexane/ethyl acetate: 4/1) to give 1.42 g(58.7%) of a colorless amorphous solid.

¹H NMR (270 MHz, CDCl₃) δ7.70–7.63 (1H, m), 7.61–7.49 (3H, m), 7.38–7.31 (2H, m), 7.30–7.20 (3H, m), 4.40–4.29 (1H, m), 3.05–3.00 (2H, m), 2.52–2.22 (4H, m), 2.13–2.09 (4H, m), 1.81–1.72 (5H, m), 1.60–1.49 (5H, m).

Preparation 2 t-Butyl 3-{1-[1-(1-Phenylcycloheptyl)-4-piperidinyl]-1H-benzimidazol-2-yl}-3,8-diazabicyclo[3.2.1]octane-8-carboxylate A mixture of 2-chloro-1-[1-(1-phenylcycloheptyl)-4-piperidinyl]-1H-benzimidazole (0.12 g, 0.294 mmol), 8-t-butoxycarbonyl-3,8-diazabicyclo[3.2.1]octane (0.12 g, 0.565 mmol,: D.Barlocco et al, *J. Med. Chem.* 1998, 41, 674), and methanol (1.5 ml) was stirred in a sealed tube at 120° C. for 4 days. After cooling down to room temperature, the reaction mixture was concentrated and purified by preparative TLC (1 mm plate×2, developed by CH₂Cl₂/MeOH: 10/1) to give 0.1269 g (74%) of an oil.

¹H NMR (300 MHz, CDCl₃) δ7.63–7.56 (1H, m), 7.56–7.45 (3H, m), 7.39–7.30(2H, m), 7.27–7.12 (3H, m), 4.40–4.09 (3H, m), 3.48–3.17 (2H, m), 3.17–2.94 (4H, m), 2.49–1.92 (12H, m), 1.86–1.40 (19H, m).

MS m/z: 583 (M⁺).

Example 1

2-(3,8-Diazabicyclo[3.2.1]oct-3-yl)-1-[1-(1-phenylcycloheptyl)-4-piperidinyl]-1H-benzimidazole A mixture of t-butyl 3-{1-[1-(1-phenylcycloheptyl)-4-piperidinyl]-1H-benzimidazol-2-yl}-3,8-diazabicyclo [3.2.1]octane-8-carboxylate (57.8 mg, 0.099 mmol), trifluoroacetic acid (1 ml), and CH₂Cl₂ (3 ml) was stirred at room temperature for 0.5 hours. After evaporation of the solvent, the residue was treated with 10% HCl solution in MeOH (1.5 ml) at room temperature and allowed to stand for 0.5 hours. The reaction mixture was concentrated to give 44.6 mg (77.6%) of white amorphous solid as an HCl salt.

¹H NMR (300 MHz, CDCl₃) δ10.90 (1H, br.s), 9.80 (1H,br.s), 9.70 (1H, br.s), 8.69 (1H, d, J=8.1 Hz), 7.95–7.80 (2H, m), 7.65–7.20 (6H, m), 4.45–4.25 (1H, m), 1H, m), 4.20–4.10 (2H, m), 3.90–1.20 (28H, m).

MS (ESI positive) m/z: 484 (M+H)⁺. IR(KBr): 3335, 2934, 2864, 2669, 2534, 1634, 1609, 1456, 1269, 1177, 1107, 978, 816, 746, 706 cm⁻¹ Anal. Calcd for C₃₁H₄₁N₅-3HCl-4.5H₂O: C, 55.23; H, 7.92; N, 10.39. Found: C, 55.37; H, 8.03; N, 10.35.

Example 2

2-(8-Methyl-3,8-diazabicyclo[3.2.1]oct-3-yl)-1-[1-(1-phenylcycloheptyl)-4-piperidinyl]-1H-benzimidazole To a stirred suspension of LiAlH₄ (17.9 mg, 0.472 mmol) in THF (1 ml) was added a solution of t-butyl 3-{1-[1-(1-phenylcycloheptyl)-4-piperidinyl]-1H-benzimidazol-2-yl}-3,8-diazabicyclo[3.2.1]octane-8-carboxylate (69.1 mg, 0.118 mmol) in THF (1 ml) at 0° C. Then the reaction mixture was refluxed for 1 day. After cooling down to room temperature, the reaction mixture was quenched by adding Na₂SO₄-10H₂O. After 1 hour of stirring, the solid was removed by filtration. The filtrate was concentrated and the residue purified by preparative TLC (1 mm plate×1, developed by CH₂Cl₂/MeOH:10/1) to give 14.1 mg (24%) of a colorless oil.

¹H NMR (300 MHz, CDCl₃) δ7.68–7.57 (1H, m), 7.57–7.42 (3H, m), 7.41–7.30 (2H, m), 7.30–7.08 (3H, m), 4.25–4.08 (1H, m), 3.48–3.34 (2H, m), 3.30–3.17 (2H, m), 3.11–2.92 (4H, m), 2.48–1.43 (25H, m). MS(ESI positive) m/z: 498(M+H)⁺.

This was converted to the HCl salt by treating with 10% HCl solution in MeOH followed by concentration to give 9.7 mg of the HCl salt as an amorphous solid. IR(KBr): 3335, 2934, 1626, 1611, 1475, 1458, 1269, 978, 748, 706 cm⁻¹ Anal. Calcd for C₃₂H₄₃N₅-3HCl-5.5H₂O: C, 54.43; H, 8.14; N, 9.92. Found: C, 54.45; H, 8.19; N, 9.81.

Example 3

4-{1-[1-(1-Phenylcycloheptyl)-4-piperidinyl]-1H-benzimidazole-2-yl}-1,4-diazaspiro[5.5]undecane A mixture of 2-chloro-1-[1-(1-phenylcycloheptyl)-4-piperidinyl]-1H-benzimidazole (0.20 g, 0.49 mmol), 1,4-diazaspiro[5.5]undecane (0.378 g, 2.45 mmol, K. P. Bφesφ et al, *J. Med. Chem.* 1995, 38, 4380), and methanol (1.5 ml) was stirred in a sealed tube at 120° C. for 2 days. After cooling down to room temperature, the reaction mixture was concentrated and purified by preparative TLC (1 mm plate× 2, developed by CH₂Cl₂/MeOH:8/1) to give 0.1277 g (50%) of colorless oil.

¹H NMR (300 MHz, CDCl₃) δ7.68–7.58 (1H, m), 7.58–7.45 (3H, m), 7.41–7.29 (2H, m), 7.29–7.09 (3H, m), 4.26–4.08 (1H, m), 3.19–2.90 (8H, m), 2.48–1.99 (8H, m), 1.92–1.32 (21H, m).

MS (EI direct) m/z: 525 (M⁺).

This was converted to the HCl salt by treating with 10% HCl solution in MeOH followed by concentration to give 34 mg of the HCl salt as an amorphous solid. IR(KBr): 3385, 2936, 2864, 2754, 2475, 1634, 1620, 1583, 1472, 1452, 1265, 1134, 754, 702 cm¹ Anal. Calcd for C₃₀H₃₉N₅-3HCl-3 H₂O: C, 56.92; H, 7.64; N, 11.06. Found: C, 56.54; H, 7.85; N, 10.79.

Example 4

1-Methyl-4-{1-[1-(1-phenylcycloheptyl)-4-piperidinyl]-1H-benzimidazole-2-yl}-1,4-diazaspiro15.5]undecane To a solution of 4-{1-[1-(1-phenylcycloheptyl)-4-piperidinyl]-1H-benzimidazole-2-yl}-1,4-diazaspiro[5.5]undecane (63.4 mg, 0.1205 mmol) and 37% formaldehyde (0.05 ml, 0.6025 mmol) in CH₃CN (1.5 ml) was added NaBH₃CN (12.1 mg, 0.1928 mmol) at room temperature. Acetic acid was added to control the pH of the reaction. After 1 hour, the reaction mixture was concentrated, basified by 2N sodium hydroxide, and extracted with CH₂Cl₂. The extracts combined were washed with brine, dried (Na₂SO₄), filtered, and concentrated. The residue was purified by preparative TLC (1 mm plate×2, developed by CH₂Cl₂/ MeOH:8/1, 2 times) to give 0.0512 g (79%) of a colorless oil.

¹H NMR (270 MHz, CDCl₃) δ7.69–7.59 (1H, m), 7.59–7.45 (3H, m), 7.41–7.30 (2H, m), 7.28–7.11 (3H, m), 4.29–4.09 (1H, m), 3.24–3.10 (4H, m), 3.09–2.94 (2H, m), 2.94–2.82 (2H, m), 2.50–1.98 (11H, m), 1.96–1.05 (20H, m).

MS (EI direct) m/z: 540 (M⁺).

This was converted to the HCl salt by treating with 10% HCl solution in MeOH followed by concentration to give 50.7 mg of HCl salt as an amorphous solid.

IR(KBr): 3393, 2934, 2864, 2665, 1628, 1614, 1578, 1474, 1134, 762, 706 cm$^{-1}$ Anal. Calcd for $C_{35}H_{49}N_5$-3HCl-4.5 $H_2O$: C, 57.57; H, 8.42; N, 9.59. Found: C, 57.69; H, 8.49; N, 9.45.

Example 5
2-[(1S,4S)-2,5-Diazabicyclo[2.2.1]hept-2-yl]-1-[1-(1-phenylcycloheptyl)-4-piperidinyl]-1H-benzimidazole A mixture of 2-chloro-1-[1-(1-phenylcycloheptyl)-4-piperidinyl]-1H-benzimidazole (0.300 g, 0.735 mmol), t-butyl (1S,4S)-(−)-2,5-diazabicyclo[2.2.1]heptane-2-carboxylate (0.7286 g, 3.675 mmol), and methanol (2.0 ml) was stirred in a sealed tube at 120° C. for 2 days. After cooling down to room temperature, the reaction mixture was concentrated and purified by preparative TLC (1 mm plate×2, developed by CH2Cl2/MeOH:10/1) to give 0.3471 g (83%) of a colorless oil.

$^1$H NMR (270 MHz, CDCl$_3$) δ7.58–7.47 (3H, m), 7.47–7.41 (1H, m), 7.39–7.29 (2H, m), 7.29–7.04 (3H, m), 4.66–4.36 (2H, m), 4.12–3.92 (1H, m), 3.87–3.57 (2H, m), 3.50–3.32 (2H, m), 3.09–2.93 (2H, m), 2.50–1.35 (29H, m).

MS (EI direct) m/z: 570 (M$^+$).

A mixture of the above prepared oil (100 mg, 0.176 mmol), trifluoroacetic acid (1.5 ml), and CH$_2$Cl$_2$ (3 ml) was stirred at room temperature for 15 hours. After evaporation of the solvent, the residue was basified with NaHCO$_3$ solution and extracted with CH$_2$Cl$_2$. The extracts combined were washed with brine, dried (Na$_2$SO$_4$), filtered, and concentrated. The residue was purified by preparative TLC (1 mm plate×1, developed by CH$_2$Cl$_2$/MeOH/NH$_4$OH:120/10/1) to give 0.0292 g (35%) of colorless oil.

$^1$H NMR (270 MHz, CDCl$_3$) δ7.58–7.47 (3H, m), 7.47–7.40 (1H, m), 7.40–7.29 (2H, m), 7.29–7.03 (3H, m), 4.34 (1H, br.s), 4.14–3.97 (1H, m), 3.76 (1H, br.s), 3.67–3.57 (1H, m), 3.38 (2H, t, J=9.1 Hz), 3.10–2.92 (3H, m), 2.50–1.88 (11H, m), 1.88–1.41 (10H, m).

MS (EI direct) m/z: 469 (M$^+$).

This product as prepared above was converted to its HCl salt by treating it with 10% HCl solution in MeOH followed by concentration to give 34 mg of the HCl salt as an amorphous solid.

IR(KBr): 3387, 2930, 2862, 2642, 2469, 1610, 1479, 1458, 1099, 746, 706 cm$^{-1}$ Anal. Calcd for $C_{30}H_{39}N_5$-3HCl-3H$_2$O: C, 56.92; H, 7.64; N, 11.06. Found: C, 56.54; H, 7.85; N, 10.79.

Example 6
2-[(1S,4S)-5-Methyl-2,5-diazabicyclo[2.2.1]hept-2-yl]-1-[1-(1-phenylcycloheptyl)-4-piperidinyl]-1H-benzimidazole The title compound was prepared according to the procedure described in Example 2 using the intermediate of Example 5. This procedure yielded 45.3 mg of white amorphous solid (53%).

$^1$H NMR (270 MHz, CDCl$_3$) δ7.56–7.46 (3H, m), 7.46–7.39 (1H, m), 7.39–7.29 (2H, m), 7.29–7.03 (3H, m), 4.29 (1H, br.s), 4.14–3.97 (1H, m), 3.67–3.58 (1H, m), 3.48–3.38 (2H, m), 3.08–2.92 (3H, m), 2.89–2.79 (1H, m), 2.53–1.99 (13H, m), 1.99–1.41 (10H, m).

MS (EI direct) m/z: 484 (M$^+$).

The compound thus prepared was converted to its HCl salt by treating it with 10% HCl solution in MeOH followed by concentration to give 51.8 mg of the HCl salt as an amorphous solid.

IR(KBr): 3385, 2932, 2650, 2532, 1611, 1479, 1458, 1101, 829, 746, 704 cm$^1$ Anal. Calcd for $C_{31}H_{41}N_5$-3HCl-3H$_2$O—CH$_3$OH: C, 56.59; H, 8.01; N, 10.31. Found C, 56.92; H, 8.25; N, 10.60.

Example 7
2-Hexahydropyrrolo[3,4-c]pyrrol-2(1H)-yl-1-[1-(1-phenylcycloheptyl)-4-piperidinyl]-1H-benzimidazole The title compound was prepared according to the procedure described in Example 5 using t-butyl hexahydropyrrolo[3,4-c]pyrrole-2(1H)-carboxylate (as prepared in S. Oida et al, JP7101959). In the de-protection step, 10% HCl solution in MeOH was used in stead of trifluoroacetic acid. Two steps overall yield was 48.5 mg (63.5%) as a colorless amorphous solid.

$^1$H NMR (270 MHz, CDCl$_3$) δ7.61–7.43 (4H, m), 7.38–7.31 (2H, m), 7.26–7.20 (1H, m), 7.18–7.10 (2H, m), 4.17–4.07 (1H, m), 3.53–3.46 (2H, m), 3.19–3.11 (4H, m), 3.03–2.98 (2H, m), 2.89–2.81 (4H, m), 2.44–2.18 (8H, m), 2.18–2.02 (3H, m), 1.81–1.68 (4H, m), 1.63–1.46 (4H, m).

This product was converted to its HCl salt by treating it with 10% HCl solution in MeOH followed by concentration to give 58 mg of the HCl salt as an amorphous solid.

MS (ESI positive) m/z: 484 (M+H)$^+$. IR (KBr): 3365, 1618, 1481 cm$^1$ Anal. Calcd for $C_{31}H_{41}N_5$-3HCl-1.1CH$_2$Cl$_2$: C, 56.16; H, 6.78; N, 10.20. Found: C, 56.06; H, 6.82; N, 10.30.

Example 8
2-(5-Methylhexahydropyrrolo[3,4-c]pyrrol-2(1H)-yl)-1-[1-(1-phenylcycloheptyl)-4-piperidinyl]-1H-benzimidazole The title compound was prepared according to the procedure described in Example 4 using 2-hexahydropyrrolo[3,4-c]pyrrol-2(1H)-yl-1-[1-(1-phenylcycloheptyl)-4-piperidinyl]-1H-benzimidazole. The reaction yielded 92.2 mg (79.5%) of a colorless amorphous solid.

$^1$H NMR (270 MHz, CDCl$_3$) δ7.60–7.43 (4H, m), 7.38–7.31 (2H, m), 7.27–7.20 (1H, m), 7.17–7.09 (2H, m), 4.20–4.06 (1H, m), 3.50–3.43 (2H, m), 3.20–3.14 (2H, m), 3.04–2.95 (4H, m), 2.88–2.79 (2H, m), 2.46–2.31 (4H, m), 2.37 (3H, s), 2.27–1.98 (8H, m), 1.82–1.47 (8H, m).

This product was converted to its HCl salt by treating it with 10% HCl solution in MeOH followed by concentration to give 108 mg of the HCl salt as an amorphous solid.

MS (ESI positive) m/z: 498 (M+H)$^+$. IR (KBr): 3365, 1615, 1460 cm$^{-1}$ Anal. Calcd for $C_{32}H_{43}N_5$-3HCl-3.5H$_2$O: C, 57.35; H, 7.97; N, 10.45. Found: C, 57.08; H, 8.12; N, 10.39.

Preparation 3
2-Chloro-1-[1-(1-methylcyclooctyl)-4-piperidinyl]-1H-benzimidazole A mixture of 4-(2-keto-1-benzimidazolinyl)piperidine (5.10 g, 23.5 mmol) and HCl solution in MeOH (20 ml) was stirred at room temperature for 10 minutes. After evaporation of the solvent, the residue was triturated in Et$_2$O to give HCl salt as off-white powder. To this HCl salt was added cyclooctanone (3.33 ml, 28.2 mmol) followed by addition of aqueous solution of KCN (1.92 g, 29.5 mmol) in water (7 ml) at room temperature. After 18 hour stirring, the resulting solid was collected by filtration, washed with water, and dried in vacuo to give 6.81 g (85.7%) of nitrile derivative as white powder. To a solution of this nitrile derivative (5.12 g, 15.1 mmol) in THF (40 ml) was added a solution of methylmagnesium bromide in Et$_2$O (3.0 M solution, 25 ml) at 0° C. Then the reaction mixture was stirred at room temperature for 18 hours. Aqueous NH$_4$Cl solution was added to the reaction mixture and the resulting solid appeared was collected by filtration, washed with water and Et$_2$O, and dried in vacuo at 70° C. to give 4.88 g (82.8%) of 1-[1-(1-methylcyclooctyl)-4-piperidinyl]-1,3-dihydro-2H-1,3-benzimidazol-2-one as white powder. A mixture of 1-[1-

(1-methylcyclooctyl)-4-piperidinyl]-1,3-dihydro-2H-1,3-benzimidazol-2-one (2.316 g, 5.95 mmol) and phosphoryl chloride (15 ml, 165.5 mmol) was heated to reflux for 1.5 h. After cooling down to room temperature, the reaction mixture was poured into ice cooled 25% ammonia solution and extracted with $CH_2Cl_2$. The extracts combined were washed with brine, dried ($Na_2SO_4$), filtered, and concentrated. The residue was purified by column chromatography (silica gel: 200 g, hexane/ethyl acetate: 4/1) to give 1.42 g(58.7%) of a colorless amorphous solid.

$^1$H NMR (300 MHz, $CDCl_3$) δ7.71–7.60 (2H, m), 7.30–72 (2H, m), 4.49–4.36 (1H, m), 3.19–3.15 (2H, m), 2.54–2.39 (2H, m), 2.30–2.21 (2H, m), 1.94–1.70 (8H, m), 1.59–1.50 (6H, m), 1.45–1.33 (2H, m), 0.89 (3H, s).

Example 9
4-{1-[1-(1-Methylcyclooctyl)-4-piperidinyl]-1H-benzimidazol-2-yl}-1,4-diazaspiro[5.5]undecane The title compound was prepared according to the procedure described in Example 3. The reaction yielded 127.7 mg (50%) of a colorless oil.

$^1$H NMR ($CDCl_3$) δ7.68–7.58 (1H, m), 7.58–7.45 (3H, m), 7.41–7.29 (2H, m), 7.29–7.09 (3H, m), 4.26–4.08 (1H, m), 3.19–2.90 (8H, m), 2.48–1.99 (8H, m), 1.92–1.31 (21H, m).

MS(EI direct) m/z: 525(M)$^+$.

The title compound converted to its HCl salt by treating with it 10% HCl solution in MeOH followed by concentration to give 156.5 mg of the HCl salt as an amorphous solid.

IR(KBr): 3393, 2934, 2860, 2752, 2480, 1628, 1610, 1582, 1458, 1379, 762, 640 cm$^{-1}$ Anal. Calcd for $C_{30}H_{47}N_5$-3HCl-2$H_2O$-1.5CH3OH: C, 56.37; H, 9.01; N, 10.43. Found: C, 56.36; H, 9.41; N, 10.77.

Example 10
2-[(1S,4R)-2,5-Diazabicyclo[2.2.1]hept-2-yl]-1-[1-(1-methylcyclooctyl)-4-piperidinyl]-1H-benzimidazole The title compound was prepared according to the procedure described in Example 5 and directly converted to HCl salt. The yield from this procedure was 109.6 mg (61%) as amorphous solid.
The corresponding methyl derivative intermediate used in the reaction:

$^1$H NMR (300 MHz, $CDCl_3$) δ7.59–7.43 (2H, m), 7.19–7.04 (2H, m), 4.69–4.40 (2H, m), 4.17–3.96 (1H, m), 3.92–3.62 (2H, m), 3.56–3.35 (2H, m), 3.23–3.04 (2H, m), 2.58–2.35 (2H, m), 2.28–2.08 (2H, m), 2.08–1.21 (27H, m), 0.86 (3H, s).

MS(EI direct) m/z: 521(M)$^+$.
HCl Salt $^1$H NMR (300 MHz, $CDCl_3$) δ10.70 (1H, br.s), 10.00 (1H, br.s), 9.45 (1H, br.s), 8.62 (1H, d, J=7.9 Hz), 7.56 (1H, d, J=7.9 Hz), 7.40–7.25 (2H, m), 4.95–4.85 (1H, m), 4.85–4.65 (1H, m), 4.62–4.55 (1H, m), 4.40–4.30 (2H, m), 3.80–3.20 (14H, m), 2.28–2.10 (4H, m), 2.00–1.40 (8H, m), 1.36 (3H, s).

MS (ESI positive) m/z: 422 (M+H)$^+$. IR(KBr): 3391, 2932, 2858, 2669, 2469, 1632, 1611, 1481, 1456, 1394, 1286, 1267, 1173, 1099, 942, 897, 826, 758, 694 cm$^1$ Anal. Calcd for $C_{26}H_{39}N_5$-3HCl-4$H_2O$: C, 51.78; H, 8.36; N, 11.61. Found: C, 51.31; H, 7.95; N, 11.43.

Example 11
2-Hexahydropyrrolo[3,4-c]pyrrol-2(1H)-yl-1-[1-(1-methylcyclooctyl)-4-piperidinyl]-1H-benzimidazole The title compound was prepared according to the procedure described in Example 7. The yield from this procedure was 68.4 mg (71.8%) as a colorless amorphous solid.

$^1$H NMR (300 MHz, $CDCl_3$) δ7.61–7.56 (1H, m), 7.53–7.48 (1H, m), 7.18–7.11 (2H, m), 4.23–4.10 (1H, m), 3.56–3.49 (2H, m), 3.19–3.14 (6H, m), 2.95–2.83 (4H, m), 2.56–2.40 (2H, m), 2.25–2.14 (8H, m), 1.91–1.32 (11H, m), 0.88 (3H, s).

MS(EI direct) m/z: 525(M)$^+$.

The product was converted to its HCl salt by treating it with 10% HCl solution in MeOH followed by concentration to give 78 mg of the HCl salt as an amorphous solid.

IR(KBr): 3396, 2930, 2718, 1639, 1616, 1481, 1458, 766 cm$^{-1}$ Anal. Calcd for $C_{27}H_{45}N_5$-3HCl-3.5$H_2O$: C, 52.98; H, 9.06; N, 11.44. Found: C, 53.23; H, 8.73; N, 11.64

Example 12
1-[1-(1-Methylcyclooctyl)-4-piperidinyl]-2-(5-methylhexahydropyrrolo[3,4-c]pyrrol-2(1H)-yl-1H-benzimidazole The title compound was prepared according to the procedure described in Example 8. The reaction yielded 81.7 mg (85.4%) as colorless amorphous solid.

$^1$H NMR (300 MHz, $CDCl_3$) δ7.60–7.49 (2H, m), 7.17–7.09 (2H, m), 4.24–4.15 (1H, m), 3.52–3.45 (2H, m), 3.23–3.14 (4H, m), 3.00–2.92 (2H, m), 2.86–2.79 (2H, m), 2.55–2.36 (7H, m), 2.24–2.07 (4H, m), 1.89–1.70 (6H, m), 1.58–1.32 (8H, m), 0.89 (3H, s).

This was converted to HCl salt by treating it with 10% HCl solution in MeOH followed by concentration to give 95 mg of HCl salt as amorphous solid. IR(KBr): 3387, 2932, 2708, 1612, 1481, 1458, 766 cm$^{-1}$ MS(ESI positive) m/z: 450(M+H)$^+$. Anal. Calcd for $C_{28}H_{43}N_5$-3HCl-3.5$H_2O$: C, 54.06; H, 8.59; N, 11.26. Found: C, 54.29; H, 8.94; N, 11.29.

Example 13
2-Hexahydropyrrolo[3,4-b]pyrrol-5(1H)-yl-1-[1-(1-methylcyclooctyl)-4-piperidinyl]-1H-benzimidazole The title compound was prepared according to the procedure described in Example 10 using 1-benzyloctahydropyrrolo[3,4-b]pyrrole (as prepared by T. Schenke et al, EP393424). In the de-protection step, hydrogenation conditions (Pd(OH)$_2$, H$_2$, MeOH) were used instead of trifluoroacetic acid. The overall yield from the two steps was 80.2 mg (55.3%) of a colorless amorphous solid.

$^1$H NMR (300 MHz, $CDCl_3$) δ7.62–7.46 (2H, m), 7.18–7.10 (2H, m), 4.25–4.12 (1H, m), 4.05–3.98 (1H, m), 3.61–3.47 (2H, m), 3.32–3.06 (5H, m), 2.99–2.84 (2H, m), 2.55–2.39 (1H, m), 2.24–2.16 (4H, m), 2.07–1.91 (2H, m), 1.86–1.69 (8H, m), 1.67–1.44 (7H, m), 1.39–1.32 (2H, m), 0.88 (3H, s).

This product was converted to its HCl salt by treating it with 10% HCl solution in MeOH followed by concentration to give 90 mg of the HCl salt as an amorphous solid.

MS (ESI positive) m/z: 436 (M+H)$^+$. IR (KBr): 3400, 2924, 2729, 1632, 1609, 1481, 1456, 762 cm$^{-1}$ Anal. Calcd for $C_{27}H_{41}N_5$-3HCl-3$H_2O$: C, 54.13; H, 8.41; N, 11.69. Found: C, 54.00; H, 8.23; N, 11.50.

Example 14
2-Hexahydropyrrolo[3,4-b]pyrrol-1(1H)-yl-1-[1-(1-methylcyclooctyl)-4-piperidinyl]-1H-benzimidazole The title compound was prepared according to the procedure described in Example 10 using t-butyl hexahydropyrrolo[3,4-b]pyrrole-5(1H)-carboxylate (as prepared by T. Schenke et al, EP393424). In a de-protection step, HCl solution in MeOH was used instead of trifluoroacetic acid. The overall yield of the two steps was 86.5 mg (71.5%) of a colorless amorphous solid.

$^1$H NMR (300 MHz, $CDCl_3$) δ7.60–7.49 (2H, m), 7.19–7.10 (2H, m), 4.63–4.57 (1H, m), 4.26–4.13 (1H, m), 3.65–3.56 (1H, m), 3.30–3.00 (4H, m), 2.95–2.81 (4H, m), 2.56–2.41 (2H, m), 2.29–2.17 (3H, m), 2.05–1.89 (3H, m), 1.84–1.69 (7H, m), 1.58–1.44 (6H, m), 1.39–1.25 (2H, m), 0.88 (3H, s).

This product was converted to its HCl salt by treating it with 10% HCl solution in MeOH followed by concentration to give 97 mg of the HCl salt as an amorphous solid.

MS (ESI positive) m/z: 436 (M+H)$^+$. IR (KBr): 3400, 2924, 2729, 1632, 1609, 1481, 1456, 762 cm$^{-1}$ Anal. Calcd for $C_{27}H_{41}N_5$-3HCl-3H$_2$O: C, 54.13; H, 8.41; N, 11.69. Found: C, 53.82; H, 8.66; N, 11.67.

Example 15
3-{1-[1-(1-Methylcyclooctyl)-4-piperidinyl]-1H-benzimidazol-2-yl}-3-azabicyclo[3.1.0]hexan-6-amine The title compound was prepared according to the procedure described in Example 14 using t-butyl 3-azabicyclo[3.1.0]hex-6-ylcarbamate (as prepared in K. E. Brighty et al, *Synlett*, 1996, 11, 1097). The overall yield from the two steps was 85.6 mg (78.3%) of a colorless amorphous solid.

$^1$H NMR (300 MHz, CDCl$_3$) δ7.55–7.45 (2H, m), 7.15–7.06 (2H, m), 4.09–3.95 (1H, m), 3.71–3.67 (2H, m), 3.59–3.55 (2H, m), 3.19–3.11 (2H, m), 2.53–2.36 (3H, m), 2.27–2.13 (2H, m), 1.92–1.70 (10H, m), 1.61–1.32 (10H, m), 0.88 (3H, s).

This product was converted to its HCl salt by treating it with 10% HCl solution in MeOH followed by concentration to give 87 mg of this HCl salt as an amorphous solid.

MS (ESI positive) m/z: 422 (M+H)$^+$. IR (KBr): 3400, 2920, 2680, 1616, 1481, 1452, 1365, 760 cm$^{-1}$ Anal. Calcd for $C_{26}H_{39}N_5$-3HCl-2.1H$_2$O: C, 54.90; H, 8.19; N, 12.31. Found: C, 55.28; H, 8.60; N, 12.21.

Example 16
2-(3,8-Diazabicyclo[3.2.1]oct-3-yl)-[1-(1-methylcyclooctyl)-4-piperidinyl]-1H-benzimidazole The title compound was prepared according to the procedure described in Example 10 using 8-t-butoxycarbonyl-3,8-diazabicyclo[3.2.1]octane (as prepared in D. Barlocco et al, *J. Med. Chem.* 1998, 41, 674). The overall yield was 179 mg (58.5%) of a colorless amorphous solid.

$^1$H NMR (300 MHz, CDCl$_3$) δ7.66–7.57 (1H, m), 7.57–7.47 (1H, m), 7.20–7.11 (2H, m), 4.35–4.17 (1H, m), 3.67–3.55 (2H, m), 3.32–3.03 (6H, m), 2.57–2.36 (2H, m), 2.27–2.11 (2H, m), 2.11–1.28 (21H, m), 0.89 (3H, s).

MS (EI direct) m/z: 435 (M$^+$).

This product was converted to its HCl salt by treating it with 10% HCl solution in MeOH followed by concentration to give 225 mg of the HCl salt of an amorphous solid.

IR (KBr): 3387, 2928, 2750, 2530, 1630, 1610, 1589, 1483, 1462, 766 cm$^{-1}$ Anal. Calcd for $C_{27}H_{41}N_5$-3HCl-2H$_2$O: C, 55.81; H, 8.33; N, 12.05. Found: C, 55.89; H, 8.45; N, 11.89.

Example 17
2-((8aS)-Hexahydropyrrolo[1,2-a]pyrazin-2(1H)-yl)-1-[1-(1-methylcyclooctyl)-4-piperidinyl]-1H-benzimidazole The title compound was prepared according to the procedure described in Example 3 using (8aS)-octahydropyrrolo[1,2-a]pyrazine (as prepared by de Costa B. R. et al, *J. Med. Chem.* 1993, 36, 2311). The reaction yielded 105 mg (79%) of a colorless amorphous solid.

$^1$H NMR (300 MHz, CDCl$_3$) δ7.70–7.60 (1H, m), 7.55–7.45 (1H, m), 7.20–7.10 (2H, m), 4.17–4.04 (1H, m), 3.49 (1H, br.d, J=11.2 Hz), 3.32 (1H, br.d, J=11.9 Hz), 3.30–3.10 (4H, m), 2.95 (1H, dd, J=10.4, 11.4 Hz), 2.60–2.40 (3H, m), 2.40–2.10 (4H, m), 2.00–1.65 (9H, m), 1.65–1.30 (12H, m), 0.87 (3H, s).

MS (EI direct) m/z: 449 (M$^+$).

The product was converted to its HCl salt by treating it with 10% HCl solution in MeOH followed by concentration to give the HCl salt as an amorphous solid. IR (KBr): 3400, 2928, 2667, 1611, 1456 cm$^{-1}$ Anal. Calcd for $C_{28}H_{43}N_5$-3HCl-$C_2H_5$OH-2.5H$_2$O: C, 55.42; H, 8.84; N, 10.77. Found: C, 55.55; H, 8.99; N, 10.63.

Example 18
2-{1-[1-(1-Methylcyclooctyl)-4-piperidinyl]-1H-benzimidazol-2-yl}octahydro-2H-pyrido[1,2-a]pyrazine The title compound was prepared according to the procedure described in Example 3 using octahydro-2H-pyrido[1,2-a]pyrazine (as prepared by de Costa B. R. et al, *J. Med. Chem.* 1993, 36, 2311). The reaction yielded 141 mg (96%) of a colorless amorphous solid.

$^1$H NMR (300 MHz, CDCl$_3$) δ7.70–7.60 (1H, m), 7.55–7.45 (1H, m), 7.20–7.10 (2H, m), 4.20–4.05 (1H, m), 3.30–3.10 (5H, m), 3.00–2.80 (3H, m), 2.60–2.30 (3H, m), 2.25–2.10 (4H, m), 2.00–1.65 (8H, m), 1.65–1.25 (14H, m), 0.88 (3H, s).

MS (EI direct) m/z: 463 (M$^+$).

This product was converted to its HCl salt by treating it with 10% HCl solution in MeOH followed by concentration to give the HCl salt of a amorphous solid.

IR (KBr): 3400, 2932, 2663, 1600, 1458 cm$^{-1}$ Anal. Calcd for $C_{29}H_{45}N_5$-3HCl-$C_2H_5$OH-2.5H$_2$O: C, 56.06; H, 8.95; N, 10.54. Found: C, 56.31; H, 9.15; N, 10.48.

Example 19
1-[1-(1-Methylcyclooctyl)-4-piperidinyl]-2-(1-methylhexahydropyrrolo[3,4-b]pyrrol-5(1H)-yl)-1H-benzimidazole The title compound was prepared according to the procedure described in Example 4 using Example 13. The procedures yielded 74.8 mg (88.1%).

$^1$H NMR (300 MHz, CDCl$_3$) δ7.58–7.49 (2H, m), 7.17–7.11 (2H, m), 4.29–4.17 (1H, m), 3.47–3.45 (2H, m), 3.39–3.25 (2H, m), 3.20–3.00 (4H, m), 2.97–2.85 (1H, m), 2.62–2.27 (4H, m), 2.43 (3H, s), 2.28–2.10 (2H, m), 1.93–1.70 (15H, m), 1.58–1.31 (2H, m), 0.88 (3H, s).

This product was converted to its HCl salt by treating it with 10% HCl solution in MeOH followed by concentration to give 89 mg of the HCl salt of an amorphous solid.

MS (ESI positive) m/z: 450 (M+H)$^+$. IR (KBr): 3390, 2920, 2655, 1625, 1480 cm$^{-1}$ Anal. Calcd for $C_{28}H_{43}N_5$-3HCl-2.1H$_2$O: C, 56.34; H, 8.48; N, 11.73. Found: C, 56.05; H, 8.64; N, 11.70.

Example 20
1-[1-(1-Methylcyclooctyl)-4-piperidinyl]-2-octahydro-2H-pyrrolo[3,4-c]pyridin-2-yl-1H-benzimidazole The title compound was prepared according to the procedure described in Example 13 using 5-benzyloctahydro-1H-pyrrolo[3,4-c]pyridine (prepared from 3,4-pyridinedicarboximide via hydrogenation, N-benzylation, and LiAlH$_4$ reduction). The overall yield of the was 66 mg (55.5%).

$^1$H NMR (300 MHz, CDCl$_3$) δ7.52–7.43 (2H, m), 7.15–7.04 (2H, m), 4.21–4.09 (1H, m), 3.74–3.46 (4H, m), 3.21–2.78 (10H, m), 2.55–2.17 (6H, m), 1.90–1.31 (15H, m), 0.90 (3H, s).

This product was converted to its HCl salt by treating it with 10% HCl solution in MeOH followed by concentration to give 71 mg of the HCl salt of an amorphous solid.

MS (ESI positive) m/z: 450 (M+H)$^+$. IR (KBr): 3390, 2925, 1620, 1485, 1450 cm$^{-1}$ Anal. Calcd for $C_{28}H_{43}N_5$-3HCl-2H$_2$O: C, 56.51; H, 8.47; N, 11.77. Found: C, 56.61; H, 8.83; N, 11.60.

Example 21
1-[1-(1-Methylcyclooctyl)-4-piperidinyl]-2-octahydro-2H-pyrrolo[3,4-c]pyridin-2-yl -1H-benzimidazole The title compound was prepared according to the procedure described in Example 11 using tert-butyl octahydro-1H-pyrrolo[3,4-b]pyridine-1-carboxylate (as prepared in EP603887). The overall yield was 86.5 mg (75.5%).

$^1$H NMR (300 MHz, CDCl$_3$) δ7.52–7.44 (2H, m), 7.14–7.03 (2H, m), 4.20–4.11 (1H, m), 3.96–3.83 (2H, m), 3.49–3.33 (2H, m), 3.19–3.04 (2H, m), 2.72–2.63 (1H, m), 2.53–2.30 (3H, m), 2.25–2.16 (2H, m), 2.00–1.31 (23H, m), 0.87 (3H, s).

This product was converted to its HCl salt by treating it with 10% HCl solution in MeOH followed by concentration to give 96 mg of the HCl salt of an amorphous solid.

MS (ESI positive) m/z: 450 (M+H)$^+$. IR (KBr): 3395, 2920, 2690, 1615, 1450 cm$^{-1}$ Anal. Calcd for C$_{28}$H$_{43}$N$_5$-3HCl-2H$_2$O: C, 56.51; H, 8.47; N, 11.77. Found: C, 56.13; H, 8.49; N, 11.41

Preparation 4
Ethyl (1SR,3aSR,6aRS)-5-benzyl-4,6-dioxooctahydro-pyrrolo[3,4-c]pyrrole-1-carboxylate A mixture of N-benzylmaleimide (2.99 g, 16 mmol), N-benzylglycine ethyl ester (6.19 g, 32 mmol), paraformaldehyde (3.83 g, 95.8 mmol), and toluene (80 ml) was heated to reflux for 2 hours. The reaction mixture was cooled down, diluted with water, and extracted with CH$_2$Cl$_2$. The extracts combined were washed with water, dried (Na$_2$SO$_4$), filtered, and concentrated. The crude product was purified by column chromatography (silica gel; 300 g, hexane/ethyl acetate:4/1) to give 5.44 g (86.8%) of colorless oil. A suspension mixture of this oil (4.00 g, 10.2 mmol), palladium hydroxide on carbon (700 mg), and methanol (60 ml) was stirred at room temperature under hydrogen atmosphere for 17 hours. After removal of the catalyst by filtration, the filtrate was concentrated and the residue was purified by column chromatography (silica gel; 250 g, CH$_2$Cl$_2$/MeOH:40/1) to give 2.69 g (87.3%) of a colorless oil.

$^1$H NMR (300 MHz, CDCl$_3$) δ7.33–7.26 (5H, m), 4.67 (2H, s), 4.23 (2H, q, J=7.3 Hz), 4.15 (1H, s), 3.62 (1H, d, J=7.3 Hz), 3.43 (1H, d, J=8.9 Hz), 3.27–3.13 (2H, m), 2.24 (1H, br.s), 1.30 (3H, t, J=7.3 Hz).

Preparation 5
t-Butyl (1SR,3aRS,6aSR)-5-benzyl-1-(hydroxymethyl)hexahydropyrrolo[3,4-c]pyrrole-2(1H)-carboxylate To a stirred suspension of LiAlH$_4$ (1.36 g, 35.8 mmol) in THF (15 ml) was added dropwise a solution of ethyl (1SR,3aSR,6aRS)-5-benzyl-4,6-dioxooctahydropyrrolo[3,4-c]pyrrole-1-carboxylate (2.69 g, 8.91 mmol) in THF (40 ml) at 0° C. Then the mixture was heated to reflux for 1 hour. The reaction mixture was cooled down and quenched with Na$_2$SO$_4$·10H$_2$O. After filtration of the reaction mixture, the filtrate was concentrated to give 2.30 g of colorless oil. To the stirred solution of this oil (2.30 g, 9.91 mmol) in CH$_2$Cl$_2$ (40 ml) was added triethylamine (1.47 ml, 10.6 mmol) followed by addition of di-tert-butyl dicarbonate (2.44 ml, 10.6 mmol) at 0° C. The resulting mixture was stirred at room temperature for 1 h. The reaction mixture was diluted with NaHCO$_3$ solution and extracted with CH$_2$Cl$_2$. The extracts combined were washed with brine, dried (Na$_2$SO$_4$), filtered, and concentrated. The crude product was purified by column chromatography (silica gel; 250 g, CH$_2$Cl$_2$/MeOH: 20/1) to give 2.31 g (78.1%) of colorless oil.

$^1$H NMR (300 MHz, CDCl$_3$) δ7.33–7.21 (5H, m), 3.86–3.84 (1H, m), 3.63–3.48 (7H, m), 2.73–2.37 (5H, m), 1.48 (9H, s).

Preparation 6
t-Butyl (1SR,3aRS,6aSR)-1-(hydroxymethyl)-5-{1-[1-(1-methylcyclooctyl)-4-piperidinyl]-1H-benzimidazol-2-yl}hexahydropyrrolo[3,4-c]pyrrole-2(1H)-carboxylate A suspension mixture of t-butyl (1SR,3aRS,6aSR)-5-benzyl-1-(hydroxymethyl)hexahydropyrrolo[3,4-c]pyrrole-2(1H)-carboxylate (2.31 g, 6.96 mmol), palladium hydroxide on carbon (404 mg), and methanol (40 ml) was stirred at room temperature under hydrogen atmosphere for 15 hours. After removal of the catalyst by filtration, the filtrate was concentrated to give 1.66 g (crude 98.6%) of a colorless oil.

A mixture of this oil (657 mg, 2.71 mmol) and 2-chloro-1-[1-(1-methylcyclooctyl)-4-piperidinyl]-1H-benzimidazole (252 mg, 0.701 mmol) in methanol (1 ml) was stirred at 120° C. in a sealed tube for 20 hours. The reaction mixture was cooled down, diluted with water, and extracted with CH$_2$Cl$_2$. The extracts combined were washed with brine, dried (Na$_2$SO$_4$), filtered, and concentrated. The crude product was purified by preparative TLC (1 mm plate'3, CH$_2$Cl$_2$/MeOH: 10/1) to give 261 mg (65.9%) of a brown amorphous solid.

$^1$H NMR (300 MHz, CDCl$_3$) δ7.57–7.47 (2H, m), 7.18–7.11 (2H, m), 4.19–4.06 (1H, m), 4.02–3.90 (1H, m), 3.83–3.61 (6H, m), 3.49–3.30 (4H, m), 3.17–3.13 (2H, m), 3.05–2.96 (1H, m), 2.74–2.64 (1H, m), 2.55–2.40 (2H, m), 2.24–2.15 (2H, m), 1.64–1.35 (8H, m), 1.47 (9H, s), 0.87 (3H, s).

Example 22
(1SR,3aRS,6aSR)-5-{1-[1-(1-Methylcyclooctyl)-4-piperidinyl]-1H-benzimidazol-2-yl}octahydropyrrolo[3,4-c]pyrrole-1-ylmethanol A mixture of t-butyl (1SR,3aRS,6aSR)-1-(hydroxymethyl)-5-{1-[1-methylcyclooctyl]-4-piperidinyl}-1H-benzimidazol-2-yl}hexahydropyrrolo[3,4-c]pyrrole-2(1H)-carboxylate (95.4 mg, 0.169 mmol) and 10% HCl solution in MeOH (2 ml) was stirred at room temperature for 15.5 hours. The reaction mixture was basified with NH$_4$OH solution and extracted with CH$_2$Cl$_2$. The extracts combined were washed with brine, dried (Na$_2$SO$_4$), filtered, and concentrated. The crude product was purified by preparative TLC (1 mm plate×1, CH$_2$Cl$_2$/MeOH/NH$_4$OH: 100/10/1) to give 70.3 mg (89.5%) of colorless amorphous solid.

$^1$H NMR (300 MHz, CDCl$_3$) δ7.60–7.56 (1H, m), 7.52–7.48 (1H, m), 7.19–7.11 (2H, m), 4.22–4.09 (1H, m), 3.70–3.64 (1H, m), 3.58–3.44 (3H, m), 3.33–3.14 (6H, m), 2.96–2.87 (2H, m), 2.68–2.58 (1H, m), 2.56–2.39 (2H, m), 2.36–2.30 (3H, m), 2.23–2.14 (2H, m), 1.92–1.69 (6H, m), 1.58–1.50 (7H, m), 1.46–1.30 (2H, m), 0.88 (3H, s).

This product was converted to its HCl salt by treating with 10% HCl solution in MeOH followed by concentration to give 74 mg of the HCl salt of an amorphous solid.

MS (ESI positive) m/z: 466 (M+H)$^+$. IR (KBr): 3380, 2940, 2680, 1610, 1480, 1450 cm$^1$ Anal. Calcd for C$_{28}$H$_{43}$N$_5$O-3HCl-2H$_2$O: C, 55.03; H, 8.25; N, 11.46. Found: C, 55.00; H, 8.09; N, 11.47

Preparation 7
t-Butyl (1SR,3aRS,6aSR)-1-(aminomethyl)-5-{1-[1-methylcyclooctyl]-4-piperidinyl}-1H-benzimidazol-2-yl}hexahydropyrrolo[3,4-c]pyrrole-2(1H)-carboxylate To a stirred solution of t-butyl (1SR,3aRS,6aSR)-1-(hydroxymethyl)-5-{1-[1-methylcyclooctyl]-4-piperidinyl}-1H-benzimidazol-2-yl}hexahydropyrrolo[3,4-c]pyrrole-2(1H)-carboxylate (230 mg, 0.407 mmol) in CH$_2$Cl$_2$ (5 ml) was added triethylamine (0.0846 ml, 0.61 mmol) and mesyl chloride (0.0473 ml, 0.611 mmol) at 0° C.

After 15 minute stirring, the reaction mixture was diluted with NaHCO$_3$ solution and extracted with CH$_2$Cl$_2$. The extracts combined were washed with brine, dried (Na$_2$SO$_4$), filtered, and concentrated to give 303 mg of colorless amorphous solid. A mixture of this mesylate (303 mg) and NaN$_3$ (80.5 mg, 1.24 mmol) in DMF (2 ml) was stirred at 70° C. for 24 h. The reaction mixture was cooled down, diluted with water, and extracted with ethyl acetate. The extracts combined were washed with water, dried (Na$_2$SO$_4$), filtered, and concentrated. The crude product was purified by preparative TLC (1 mm plate×2, hexane/acetone: 3/2) to give 193 mg (80.4%) of a colorless amorphous solid.

$^1$H NMR (300 MHz, CDCl$_3$) δ7.57–7.53 (1H, m), 7.50–7.46 (1H, m), 7.18–7.08 (2H, m), 4.19–4.05 (1H, m), 4.06–3.90 (1H, m), 3.81–3.64 (2H, m), 3.44–3.27 (6H, m), 3.20–3.06 (3H, m), 2.96–2.86 (1H, m), 2.54–2.40 (2H, m), 2.24–2.16 (2H, m), 1.85–1.69 (6H, m), 1.58–1.54 (8H, m), 1.47 (9H, s), 1.47–1.25 (2H, m), 0.87 (3H, s).

A mixture of this solid (192 mg, 0.325 mmol), palladium black (48.3 mg), methanol (4 ml), and THF (1 ml) was stirred at room temperature under hydrogen atmosphere for 18.5 hours. After removal of the catalyst by filtration, the filtrate was concentrated and the residue was purified by preparative TLC (1 mm plate×2, CH$_2$Cl$_2$/MeOH/NH$_4$OH: 100/10/1) to give 156 mg (83.4%) of a colorless amorphous solid. This amine was used for next reaction without purification.

Example 23

N-[(1SR,3aRS,6aSR)-5-{1-[1-(1-Methylcyclooctyl)-4-piperidinyl]-1H-benzimidazol-2-yl}octahydropyrrolo [3,4-c]pyrrole-1-ylmethyl]methanesulfonamide To a stirred solution of t-butyl (1SR,3aRS,6aSR)-1-(aminomethyl)-5-{1-[1-methylcyclooctyl]-4-piperidinyl}-1H-benzimidazol-2-yl}hexahydropyrrolo[3,4-c]pyrrole-2(1H)-carboxylate (66.4 mg, 0.118 mmol) was added triethylamine (0.0244 ml, 0.176 mmol) and mesyl chloride (0.0137 ml, 0.177 mmol) at room temperature. After 30 min stirring at room temperature, the reaction mixture was basified with NaHCO$_3$ solution and extracted with CH$_2$Cl$_2$. The extracts combined were washed with brine, dried (Na$_2$SO$_4$), filtered, and concentrated. The crude product was purified by preparative TLC (1 mm plate×1, CH2Cl2/MeOH: 10/1) to give 71.7 mg (94.9%) of a colorless amorphous solid.

$^1$H NMR (300 MHz, CDCl$_3$) δ7.56–7.47 (2H, m), 7.18–7.09 (2H, m), 5.61–5.54 (1H, m), 4.18–4.07 (1H, m), 4.03.70–3.96 (1H, m), 3.81–3.75 (2H, m), 3.68–3.60 (1H, m), 3.49–3.25 (3H, m), 3.20–3.05 (2H, m), 2.95 (3H, s), 2.96–2.82 (1H, m), 2.53–2.41 (2H, m), 2.25–2.16 (2H, m), 1.91–1.69 (8H, m), 1.47 (9H, s), 1.91–1.22 (11H, m), 0.87 (3H, s).

A mixture of this methanesulfonamide derivative (71.7 mg, 0.112 mmol) and 10% HCl solution in MeOH (2 ml) was stirred at room temperature for 15 hours. The reaction mixture was basified with NH$_4$OH solution and extracted with CH$_2$Cl$_2$. The extracts combined were washed with brine, dried (Na2SO4), filtered, and concentrated. The crude product was purified by preparative TLC (1 mm plate×1, CH$_2$Cl$_2$/MeOH/NH$_4$OH: 100/10/1) to give 53.0 mg (87.6%) of colorless amorphous solid.

$^1$H NMR (300 MHz, CDCl$_3$) δ7.60–7.50 (2H, m), 7.17–7.11 (2H, m), 4.21–4.09 (1H, m), 3.57–3.45 (2H, m), 2.98 (3H, s), 3.32–2.84 (10H, m), 2.65–2.40 (3H, m), 2.29–2.17 (2H, m), 1.92–1.71 (6H, m), 1.67–1.33 (10H, m), 0.90 (3H, s).

This product was converted to its HCl salt by treating with 10% HCl solution in MeOH followed by concentration to give 55 mg of the HCl salt as an amorphous solid.

MS (ESI positive) m/z: 543 (M+H)$^+$. IR (KBr): 3405, 2925, 2680, 1615, 1460 cm$^{-1}$ Anal. Calcd for C$_{29}$H$_{46}$N$_6$O$_2$-3HCl-1.1H$_2$O: C, 51.83; H, 7.68; N, 12.51. Found: C, 51.43; H, 7.82; N, 12.16

Example 24

N-[(1SR,3aRS,6aSR)-5-{1-[1-(1-Methylcyclooctyl)-4-piperidinyl]-1H-benzimidazol-2-yl}octahydropyrrolo[3,4-c]pyrrole-1-ylmethyl]urea To a stirred solution of t-butyl (1SR,3aRS,6aSR)-1-(aminomethyl)-5-{1-[1-methylcyclooctyl]-4-piperidinyl}-1H-benzimidazol-2-yl}hexahydropyrrolo[3,4-c]pyrrole-2(1H)-carboxylate (88.7 mg, 0.157 mmol) in THF (3 ml) was added 1,1'-carbonyldiimidazole (127 mg, 0.783 mmol) at room temperature. After 1 hour stirring at room temperature, the reaction mixture was dilute with water and extracted with ethyl acetate. The extracts combined were washed with brine, dried (Na$_2$SO$_4$), filtered, and concentrated. To a solution of this crude product in THF (2 ml) was added 25% NH$_4$OH solution (1 ml) at room temperature. After 3 days stirring at room temperature, the reaction mixture was diluted with NH$_4$OH and extracted with ethyl acetate. The extracts combined were washed with brine, dried (Na$_2$SO$_4$), filtered, and concentrated. Crude product was purified by preparative TLC (1 mm plate×1, CH$_2$Cl$_2$/MeOH/NH$_4$OH: 100/10/1) to give 77.3 mg (81.0%) of colorless amorphous solid.

$^1$H NMR (300 MHz, CDCl$_3$) δ7.56–7.46 (2H, m), 7.17–7.11 (2H, m), 5.90–5.83 (1H, m), 4.82–4.72 (2H, m), 4.18–4.04 (1H, m), 4.00–3.87 (1H, m), 3.82–3.71 (2H, m), 3.67–3.59 (1H, m), 3.39–3.25 (6H, m), 3.20–2.99 (3H, m), 2.89–2.78 (1H, m), 2.54–2.38 (2H, m), 2.24–2.15 (2H, m), 1.91–1.32 (18H, m), 1.45 (9H, s).

A mixture of this urea derivative (77.3 mg, 0.127 mmol) and 10% HCl solution in MeOH (2 ml) was stirred at room temperature for 23 hours. The reaction mixture was concentrated and dried at 45° C. to give 55 mg of the HCl salt as an amorphous solid.

$^1$H NMR (300 MHz, DMSO-d6) δ10.63 (2H, br.s), 10.51 (1H, br.s), 9.58 (1H, br.s), 8.61 (1H, d, J=8.1 Hz), 7.54 (1H, d, J=8.1 Hz), 7.40–7.25 (2H, m), 6.70–6.60 (1H, m), 5.10–4.92 (1H, m), 4.15–3.85 (4H, m), 3.80–3.20 (12H, m), 3.05–2.93 (1H, m), 2.30–2.00 (4H, m), 1.92–1.40 (14H, m), 1.39 (3H, s).

MS (ESI positive) m/z: 508 (M+H)$^+$. IR (KBr): 3335, 2930, 2685, 1615, 1540, 1480 cm$^{-1}$ Anal. Calcd for C$_{29}$H$_{45}$N$_7$O-3HCl-4H$_2$O: C, 50.54; H, 8.19; N, 14.23. Found: C, 50.74; H, 7.96; N, 14.10.

Example 25

2-Methyl-5-{1-[1-(1-methylcyclooctyl)-4-piperidinyl]-1H-benzimidazol-2-yl}tetrahydropyrrolo[3,4-c]pyrrole-1,3(2H, 3aH)-dione The title compound was prepared according to the procedure described in Example 3 using 2-methyltetrahydropyrrolo[3,4-c]pyrrole-1,3(2H, 3aH)-dione (as prepared by M. Joucla et al in *Bull. Soc. Chim. Fr.* 579–83, 1988). The overall yield of the two steps was 129 mg (98.5%).

$^1$H NMR (300 MHz, CDCl$_3$) δ7.63–7.56 (1H, m), 7.54–7.48 (1H, m), 7.21–7.14 (2H, m), 4.00–3.86 (1H, m), 3.85–3.81 (2H, m), 3.53–3.41 (4H, m), 3.19–3.11 (2H, m), 3.05 (3H, s), 2.47–2.33 (2H, m), 2.18–2.10 (2H, m), 1.89–1.68 (6H, m), 1.57–1.4 (8H, m), 1.39–1.31 (2H, m), 0.89 (3H, s).

This product was converted to its HCl salt by treating with 10% HCl solution in MeOH followed by concentration to give 150 mg of the HCl salt as an amorphous solid.

MS (ESI positive) m/z: 478 (M+H)⁺. IR (KBr): 3370, 2930, 2860, 1700, 1610, 1480 cm⁻¹ Anal. Calcd for $C_{28}H_{39}N_5O_2$·2HCl·1.5H$_2$O: C, 58.23; H, 7.68; N, 12.12. Found: C, 58.11; H, 7.85; N, 11.96.

Preparation 8
1-Benzyl-2-methyloctahydropyrrolo [3,4-b]pyrrole

A mixture of ethyl allyl(2-oxoethyl)carbamate (1.27 g, 7.43 mmol), N-benzylalanine (1.34 g, 7.49 mmol) and toluene (25 ml) was stirred at 120° C. for 6 hours. After cooling down to room temperature, the reaction mixture was diluted with NaHCO₃ solution and extracted with ethyl acetate. The extracts combined were washed with brine, dried (Na₂SO₄), filtered, and concentrated. The crude product was purified by column chromatography (silica gel: 150 g, hexane/ethyl acetate:3/2 as an eluent) to give 1.32 g (61.7%) of yellow oil.

¹H NMR (270 MHz, CDCl₃) δ7.37–7.19 (5H, m), 4.12 (2H, q, J=7.0 Hz), 3.87 (1H, d, J=13.5 Hz), 3.60–3.39 (5H, m), 3.19–3.04 (2H, m), 2.83–2.70 (1H, m), 1.80–1.73 (2H, m), 1.26 (3H, t, J=7.0 Hz), 1.03 (3H, d, J=6.2 Hz).

A mixture of this oil (1.32 g, 4.58 mmol) and c-HCl (15 ml) was refluxed for 24 hours. The reaction mixture was cooled down, basified with NaHCO₃ solution, and extracted with CH₂Cl₂. The extracts combined were washed with brine, dried (Na₂SO₄), filtered, and concentrated to give 687 mg (69.4%) of title compound which was used in the next reaction without purification.

¹H NMR (300 MHz, CDCl₃) δ7.36–7.22 (5H, m), 3.79 (1H, d, J=13.2 Hz), 3.58 (1H, d, J=13.2 Hz), 3.38–3.33 (1H, m), 3.19–3.09 (1H, m), 3.10–2.98 (2H, m), 2.87–2.73 (2H, m), 2.52–2.45 (1H, m), 1.79–1.70 (1H, m), 1.62–1.53 (1H, m), 0.94 (3H, d, J=6.3 Hz).

Example 26
1-[1-(1-Methylcyclooctyl)-4-piperidinyl]-2-(2-methylhexahydropyrrolo[3,4-b]pyrrole-5(1H)-yl)-1H-benzimidazole The title compound was prepared according to the procedure described in Example 13 using 1-benzyl-2-methyloctahydropyrrolo [3,4-b]pyrrole (as prepared in Preparation 8). The overall yield of the two steps was 69.1 mg (55.3%).

¹H NMR (300 MHz, CDCl₃) δ7.60–7.48 (2H, m), 7.18–7.12 (2H, m), 4.18–4.10 (1H, m), 3.65–3.41 (3H, m), 3.20–3.15 (4H, m), 3.02–2.93 (1H, m), 2.53–2.42 (2H, m), 2.24–2.16 (4H, m), 1.84–1.69 (8H, m), 1.58–1.38 (10H, m), 1.21 (3H, d, J=6.3 Hz), 0.88 (3H, s).

This product was converted to its HCl salt by treating it with 10% HCl solution in MeOH followed by concentration to give 73 mg of the HCl salt as an amorphous solid.

MS (ESI positive) m/z: 450 (M+H)⁺. IR (KBr): 3380, 2925, 2860, 2690, 1615, 1455 cm⁻¹ Anal. Calcd for $C_{28}H_{43}N_5$·3HCl·1.6H$_2$O: C, 57.21; H, 8.44; N, 11.91. Found: C, 56.94; H, 8.46; N, 11.68.

Preparation 9
Methyl 1-[1-(1-Phenylcycloheptyl)-4-piperidinyl]-1H-benzimidazole-2-carboxylate To a stirred solution of 1-[1-(1-phenylcycloheptyl)-4-piperidinyl]-1H-benzimidazole (as prepared in WO 00/008013, 7.828 g, 20.957 mmol) in THF (200 ml) and HMPA (70 ml) was added dropwise a solution of n-BuLi (1.54 M solution in hexane, 20.4 ml, 31.435 mmol) at −78° C. After 1 hour stirring at −78° C., methyl cyanoformate was added to the reaction mixture at −78° C. After 2 hours stirring, the reaction mixture was quenched with NH₄Cl solution and warmed to room temperature. The reaction mixture was extracted with ethyl acetate. The extracts combined were washed with NaHCO₃ solution and brine, dried (Na₂SO₄), filtered, and concentrated to give oil. This oil was purified by column chromatography (silica gel:200 g, ethyl acetate/n-hexane:1/2 as an eluent) to afford 1.53 g (17%) of title compound as colorless foam.

¹H NMR (300 MHz, CDCl₃) δ7.87 (1H, d, J=7.9 Hz), 7.77 (1H, d, J=8.0 Hz), 7.60–7.45 (2H, m), 7.40–7.20 (5H, m), 5.50–5.35 (1H, m), 4.02 (3H, s), 3.10–2.95 (2H, m), 2.50–2.25 (4H, m), 2.20–1.95 (4H, m), 1.90–1.70 (4H, m), 1.70–1.45 (6H, m),

MS (EI direct) m/z: 431 (M⁺), 374(100%).

Preparation 10
1-[1-(1-Phenylcycloheptyl)-4-piperidinyl]-1H-benzimidazole-2-carbaldehyde To a stirred solution of methyl 1-[1-(1-phenylcycloheptyl)-4-piperidinyl]-1H-benzimidazole-2-carboxylate (this was prepared in preparation 9, 1.13 g, 2.62 mmol) in THF (25 ml) was added LiAlH₄ (794 mg, 20.95 mmol) at −78° C. After 4 hour stirring at −78° C., the reaction mixture was quenched with Na₂SO₄·10H₂O and KF and the resulting suspension mixture was diluted with CH₂Cl₂. After filtration, the filtrate was concentrated to give 1.098 g of colorless foam. To a stirred solution of this colorless foam (1.098 g) in CH₂Cl₂ (30 ml) was added MnO₂ (4.73 g) and resulting mixture was stirred at room temperature for 18 hours. The reaction mixture was diluted with CH₂Cl₂ and filtered. The filtrate was concentrated and purified by column chromatography (silica gel:80 g, ethyl acetate/n-hexane:1/3 as an eluent) to afford 603 mg (57%) of title compound as colorless foam.

¹H NMR (270 MHz, CDCl₃) δ10.09 (1H, s), 7.93–7.88 (1H, m), 7.79–7.74 (1H, m), 7.56–7.50 (2H, m), 7.47–7.30 (4H, m), 7.27–7.17 (1H, m), 5.52–5.36 (1H, m), 3.08–2.90 (2H, m), 2.45–2.25 (4H, m), 2.15–2.06 (4H, m), 1.90–1.70 (4H, m), 1.65–1.45 (6H, m).

Preparation 11
tert-Butyl 5-({1-[1-(1-Phenylcycloheptyl)-4-piperidinyl]-1H-benzimidazole-2-yl}methyl)-2,5-diazabicyclo[2.2.1]heptane-2-carboxylate To a stirred solution of 1-[1-(1-phenylcycloheptyl)-4-piperidinyl]-1H-benzimidazole-2-carbaldehyde (this was prepared in preparation 10, 159 mg, 0.396 mmol) and t-butyl (1S,4S)-(−)-2,5-diazabicyclo[2.2.1]heptane-2-carboxylate (86 mg, 0.436 mmol) in 1,2-dichloroethane (4 ml) was added NaBH(OAc)₃ (117 mg, 0.554 mmol) and acetic acid (48 μl, 0.832 mmol) at room temperature. After 24 hour stirring, the reaction mixture was quenched with NaHCO₃ solution and extracted with CH₂Cl₂. The extracts combined were dried over Na₂SO₄, filtered, and concentrated. The residue was purified by preparative TLC (1 mm thick plate×2, acetone/n-hexane:1/3) to afford 227 mg (98%) of title compound as colorless foam.

¹H NMR (300 MHz, CDCl₃) δ7.73–7.68 (1H, m), 7.64–7.59 (1H, m), 7.55–7.50 (2H, m), 7.38–7.17 (5H, m), 4.60–4.40 (1H, m), 4.38 (0.5H, br.s), 4.26 (0.5H, br.s), 4.04–3.85 (2H, m), 3.50–3.30 (2H, m), 3.25–3.08 (1H, m), 3.05–2.95 (2H, m), 2.95–2.72 (2H, m), 2.45–2.17 (4H, m), 2.14–2.05 (4H, m), 1.90–1.46 (12H, m), 1.44 (9H, s).

MS (EI direct) m/z: 583 (M⁺), 510, 372, 329(100%), 273, 214, 91.

Example 27
(1S,4S)-2-[(5-Methyl-2,5-diazabicyclo[2.2.1]hept-2-yl)methyl]-1-[1-(1-phenylcycloheptyl)-4-piperidinyl]-1H-benzimidazole To a stirred solution tert-butyl 5-({1-[1-(1-phenylcycloheptyl)-4-piperidinyl]-1H-benzimidazole-2-yl}methyl)-2,5-diazabicyclo[2.2.1]heptane-2-carboxylate (this was prepared in preparation 11, 227 mg, 0.39 mmol) in $CH_2Cl_2$ (5 ml) was added trifluoroacetic acid (2.5 ml) at room temperature. After 2hour stirring, 10% HCl solution in MeOH was added to the reaction mixture and concentrated to give oil. To this oil was added EtOH and toluene and evaporated to remove excess trifluoroacetic acid. This oil was basified with 25% $NH_4OH$ solution and extracted with $CH_2Cl_2$. The extracts combined were dried ($Na_2SO_4$), filtered, and concentrated to give 142 mg of pale yellow foam. To a stirred solution of this crude amine derivative (142 mg, 0.294 mmol) and 36% formalin (49 µl, 0.587 mmol) in MeCN (5 ml) was added $NaBH_3CN$ (24 mg, 0.382 mmol) at room temperature. 10% HCl solution in MeOH was added to the reaction mixture to adjust the pH around 4. After overnight stirring, the reaction mixture was basified with $NaHCO_3$ solution and extracted with $CH_2C_2$. The extracts combined were dried ($Na_2SO_4$), filtered, and concentrated. The residue was purified by preparative TLC (1 mm thick plate×2, $CH_2Cl_2$/MeOH/25%/$NH_4OH$:100/10/1) to afford 90 mg (62%) of title compound as off white solid.

$^1$H NMR (300 MHz, $CDCl_3$) δ7.73–7.60 (2H, m), 7.60–7.50 (2H, m), 7.38–7.10 (5H, m), 4.60–4.54 (1H, m), 4.00 (1H, d, J=13.4 Hz), 3.87 (1H, d, J=13.4 Hz), 3.41 (1H, s), 3.28 (1H, s), 3.07–2.97 (3H, m), 2.84–2.64 (31H, m), 2.45 (3H, s), 2.44–2.20 (4H, m), 2.15–2.07 (4H, m), 1.90–1.70 (6H, m), 1.68–1.45 (6H, m).

This product was converted to its HCl salt by treating with 10% HCl solution in MeOH followed by concentration to give 70 mg of the HCl salt as an amorphous solid.

MS (ESI positive) m/z: 498 (M+H)$^+$. IR (KBr): 3400, 2934, 2361, 1624, 1458 cm$^{-1}$ Anal. Calcd for $C_{32}H_{43}N_5$-3HCl-4.3$H_2O$: C, 56.14; H, 8.04; N, 10.23. Found: C, 56.15; H, 8.29; N, 10.09.

Example 28
2-[(8-Methyl-8-azabicyclo[3.2.1]oct-3-yl)oxy]-1-[1-(1-methylcyclooctyl)-4-piperidinyl]-1H-benzimidazole To a stirred suspension of NaH (60% oil suspension, 102.8 mg, 2.57 mmol was used after washing with n-hexane) in DMF (1.5 ml) was added a solution of tropine (190.6 mg, 1.35 mmol) in DMF (1.5 ml) dropwise at 0° C. After 0.5 hour stirring, a solution of 2-chloro-1-[1-(1-methylcyclooctyl)-4-piperidinyl]-1H-benzimidazole (162 mg, 0.45 mmol) in DMF (3 ml) was added to the reaction mixture at 0° C. The resulting mixture was stirred at room temperature for 23 hours and then at 120° C. for 19 hours. After cooling down to 0° C., the reaction mixture was quenched with water and extracted with $CH_2Cl_2$. The extracts combined were washed with brine, dried ($Na_2SO_4$), filtered, and concentrated to give 391.1 mg of crude oil, which was purified by preparative TLC (1 mm thick plate×3, $CH_2Cl_2$/MeOH:10/1) to afford 42.3 mg (20%) of title compound as a brown oil.

$^1$H NMR (300 MHz, $CDCl_3$) δ7.57–7.48 (1H, m), 7.36–7.30 (1H, m), 7.17–7.08 (2H, m), 5.39–5.33 (1H, m), 4.20–4.06 (1H, m), 3.24–3.10 (4H, m), 2.50–2.00 (18H, m, including 3H, s at 2.34 ppm), 1.95–1.25 (13H, m), 0.87 (3H, s).

This product was converted to its HCl salt by treating with 10% HCl solution in MeOH followed by concentration to give 42.5 mg of the HCl salt as an yellow solid (mp 246.6° C.).

MS (ESI positive) m/z: 465 (M+H)$^+$. IR (KBr): 2923, 2361, 1699, 1488 cm$^{-1}$ Anal. Calcd for $C_{29}H_{44}N_4O$-2HCl-3$H_2O$: C, 58.87; H, 8.86; N, 9.47. Found: C, 59.11; H, 8.84; N, 9.32.

Example 29 and 30
(3,7-trans)-1-{1-[1-(1-Methylcyclooctyl)-4-piperidinyl]-1H-benzimidazole-2-yl}octahydro-2H-bezimidazol-2-one and (3,7-cis)-1-{1-[1-(1-Methylcyclooctyl)-4-piperidinyl]-1H-benzimidazole-2-yl}octahydro-2H-bezimidazol-2-one A mixture of 2-chloro-1-[1-(1-methylcyclooctyl)-4-piperidinyl]-1H-benzimidazole (150 mg, 0.417 mmol) and 1,2-cyclohexanediamine (476 mg, 4.167 mmol) in MeOH (0.5 ml) was heated to 120° C. in a sealed tube for 2 days. After cooling down to room temperature, the reaction mixture was concentrated and the residue was purified by preparative TLC (1 mm thick plate×2, $CH_2Cl_2$/MeOH/$NH_4OH$:100/10/1) to afford 113.9 mg of yellow amorphous solid. To a stirred solution of this solid (113.9 mg, 0.26 mmol) in benzene (5 ml) was added triphosgene (100 mg, 0.338 mmol) at room temperature and the resulting mixture was refluxed for 15 hours. After cooling down to room temperature, the reaction mixture was quenched with $NaHCO_3$ solution and extracted with $CH_2Cl_2$. The extracts combined were washed with brine, dried ($Na_2SO_4$), filtered, and concentrated. The residue was purified by preparative TLC (1 mm thick plate×2, $CH_2Cl_2$/MeOH/$NH_4OH$:120/12/1) to afford 32.1 mg (27%) of title compound (trans) and 22.5 mg (19%) of title compound (cis) as a white amorphous solid.

Trans Isomer $^1$H NMR (270 MHz, $CDCl_3$) δ7.74–7.60 (2H, m), 7.28–7.15 (2H, m), 5.63–5.50 (1H, m), 4.39–4.20 (1H, m), 3.98 (1H, dt, J=11.0, 3.1 Hz), 3.44–3.29 (1H, m), 3.21–3.00 (2H, m), 2.56–1.27 (28H, m), 0.87 (3H, s).

This product was converted to its HCl salt by treating with 10% HCl solution in MeOH followed by concentration to give 34.9 mg of the HCl salt as a white amorphous solid.

MS (ESI positive) m/z: 464 (M+H)$^+$. IR (KBr): 3387, 2937, 1747, 1645, 1576, 1479, 1391, 1306, 1256, 760 cm$^{-1}$ Anal. Calcd for $C_{28}H_{41}N_5O$-HCl-2.9$H_2O$: C, 58.96; H, 8.80; N, 12.28. Found: C, 58.60; H, 8.30; N, 12.19.

Cis Isomer $^1$H NMR (270 MHz, $CDCl_3$) δ7.74–7.63 (2H, m), 7.28–7.18 (2H, m), 5.56–5.44 (1H, m), 4.70–4.58 (1H, m), 4.37–4.18 (1H, m), 3.76–3.63 (1H, m), 3.24–3.04 (2H, m), 2.58–1.10 (28H, m), 0.87 (3H, s).

This product was converted to its HCl salt by treating with 10% HCl solution in MeOH followed by concentration to give 25.1 mg of the HCl salt as a white amorphous solid.

MS (ESI positive) m/z: 464 (M+H)$^+$. IR (KBr): 2934, 1744, 1626, 1574, 1477, 1387, 1306, 1269, 762 cm$^{-1}$ Anal. Calcd for $C_{28}H_{41}N_5O$-HCl-2.5$H_2O$-0.5CH2C12: C, 58.25; H, 8.23; N, 11.92. Found: C, 58.03; H, 8.14; N, 12.05.

The compounds of this invention represented by Formula (I), wherein $Z^1$ through $Z^4$ are all hydrogen, prepared in the above working examples are summarized in the following table.

TABLE
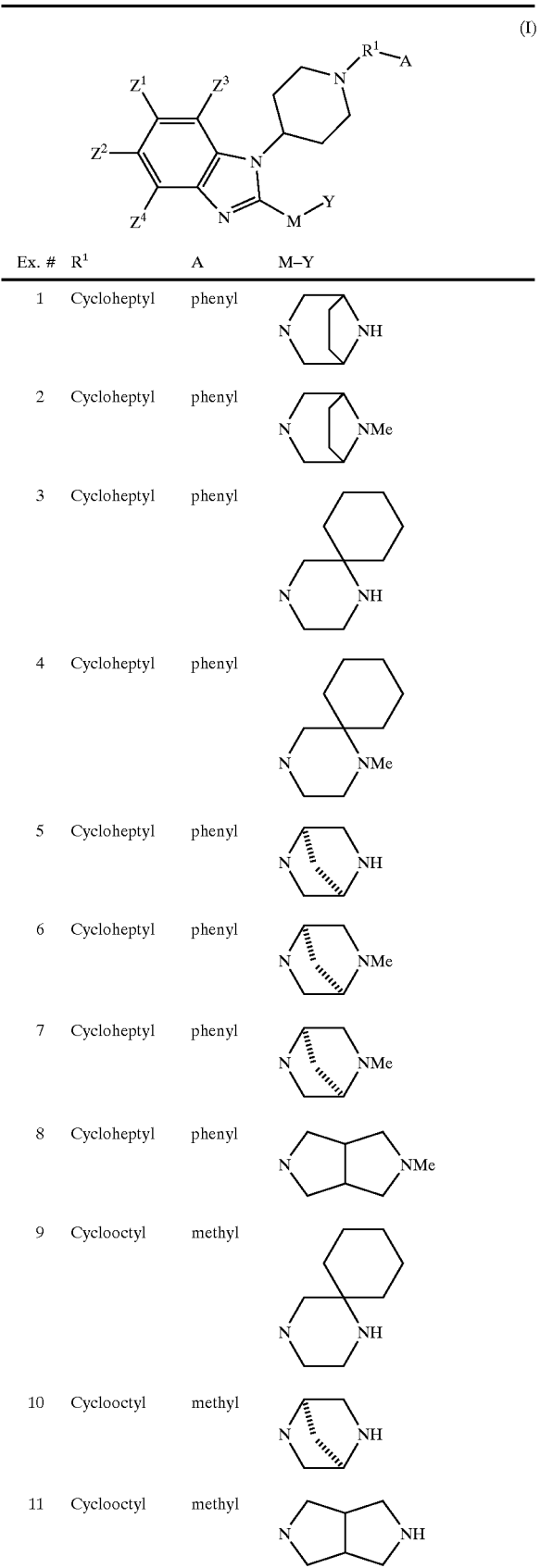
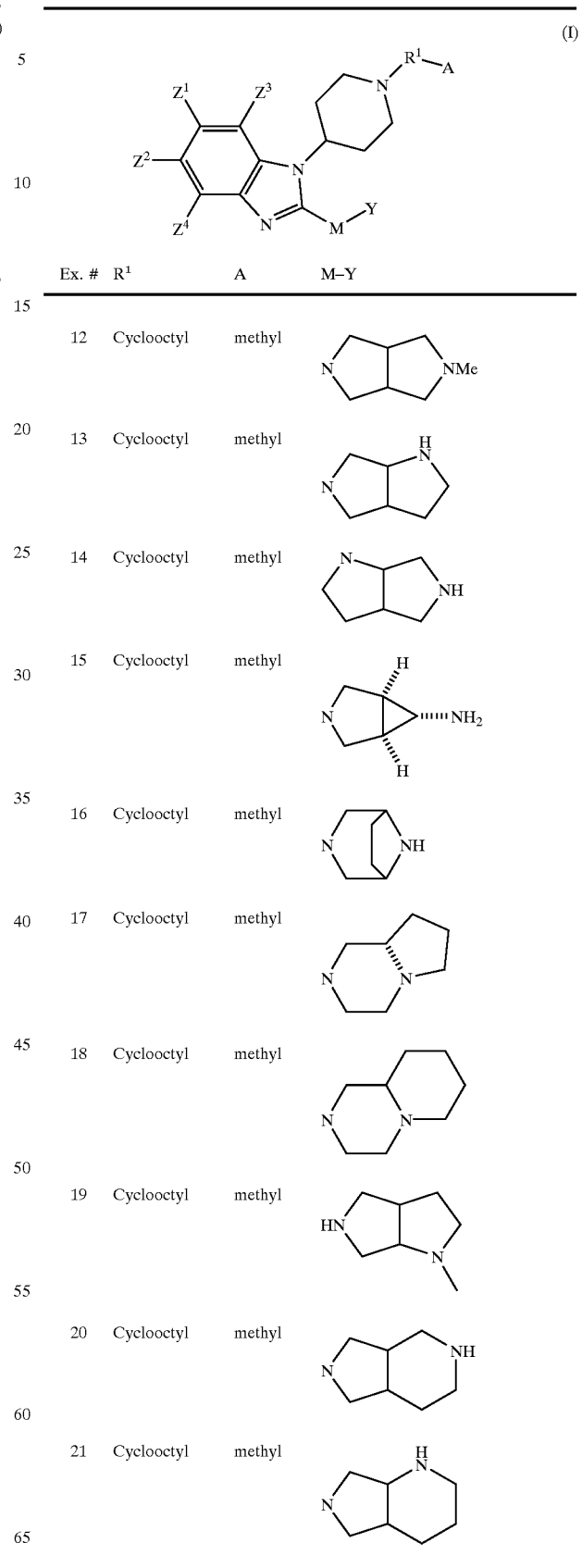

TABLE-continued

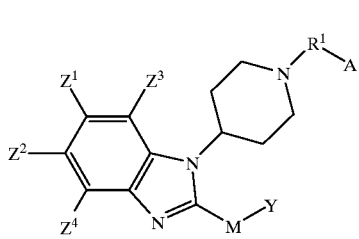

(I)

| Ex. # | R¹ | A | M–Y |
|---|---|---|---|
| 22 | Cyclooctyl | methyl | 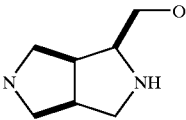 |
| 23 | Cyclooctyl | methyl | 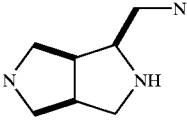 |
| 24 | Cyclooctyl | methyl | 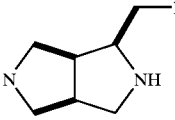 |
| 25 | Cyclooctyl | methyl | 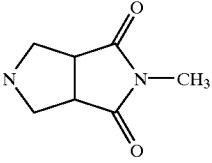 |
| 26 | Cyclooctyl | methyl | 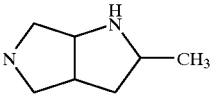 |
| 27 | Cycloheptyl | phenyl | 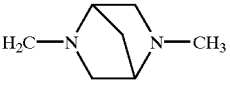 |
| 28 | Cyclooctyl | methyl |  |
| 29 | Cyclooctyl | methyl | 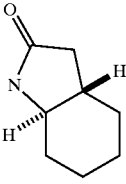 |
| 30 | Cyclooctyl | methyl | 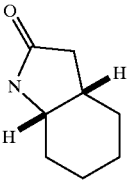 |

What is claimed is:

1. A compound of the following formula:

(I)

or a salt thereof, wherein

R¹ is selected from the group consisting of $(C_3-C_{11})$ cycloalkyl, $(C_6-C_{16})$bicycloalkyl, $(C_6-C_{16})$ tricycloalkyl and $(C_8-C_{16})$tetracyclyoalkyl, wherein said groups are partially saturated, fully saturated or fully unsaturated and are optionally substituted with 1 to 3 substituents independently selected from the group consisting of halo, hydroxy, $(C_1-C_5)$alkyl and $(C_3-C_7)$ cycloalkyl;

A is attached to the same carbon acorn of R¹, that is also attached to he nitrogen atom of the piperidine ring, and is selected from the group consisting of $(C_1-C_7)$alkyl optionally substituted with 1 to 3 halo; $(C_2-C_5)$alkenyl; $(C_2-C_5)$alkynyl; phenyl-$(C_1-C_5)$alkyl optionally substituted at the phenyl moiety with 1 to 3 substituents; hydroxy-$(C_1-C_4)$alkyl; $(C_3-C_4)$alkoxy-$(C=O)$; aryl optionally substituted with 1 to 3 substituents; and an aromatic or non-aromatic heterocyclic ring comprising four to ten ring atoms wherein one to four ring atoms are independently selected from nitrogen, oxygen and sulfur and said aromatic or non-aromatic heterocyclic ring is optionally substituted with 1 to 3 substituents, and the phenyl moiety in the substituents attached to said phenyl moiety in the phenyl-$(C_1-C_4)$alkyl, aryl, or heterocyclic ring is optionally substituted with 1 to 3 substituents independently selected from the group consisting of halo; hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—; phenyl; benzyl; —CHO; cyano; $(C_1-C_4)$alkyl-CO—; $NH_2$—CO—; $NH_2$—$CH_2$—; amino; $(C_1-C_4)$alkyl-NH—; di[$(C_1-C_4)$alkyl ]-N—; $(C_1-C_4)$alkyl-CO—NH—; $(C_1-C_4)$alkyl-NH—CO—; hydrazino; azido; ureido; amidino; guanidino; oxo and =N—OH;

M is selected from the group consisting of a single covalent bond, $CH_2$, O, S, SO, $SO_2$, CO, NH, N[$(C_1-C_6)$alkyl ], CONH and NHCO;

Y is selected from the following:

(a) 4- to 12-membered bicyclic-carbocyclic rings wherein said bicyclic-carbocyclic rings are optionally substituted with 1 to 6 substituents independently selected from the group consisting of halo, hydroxy, $(C_1-C_4)$ alkyl optionally substituted with 1 to 3 halo; $(C_1-C_4)$ alkoxy optionally substituted with 1 to 3 halo; $(C_1-C_4)$ alkyl-CO—; phenyl; benzyl; —CHO; cyano; $(C_1-C_4)$ alkyl-CO—; $NH_2$—CO—; $NH_2$—$CH_2$—; amino; $(C_1-C_4)$alkyl-NH—; di[$(C_1-C_4)$alkyl ]-N—; $(C_1-C_4)$ alkyl-CO—NH—; $(C_1-C_4)$alkyl-NH—CO—; hydrazino; azido; ureido: amidino; guanidino; oxo and =N—OH, wherein the optionally substituted $(C_1-C_4)$ alkyl are attached to the carbon or nitrogen atoms and other substituents are attached to the carbon atoms in the bicycle-heterocyclic ring; with the proviso that said bicyclic-carbocyclic ring is not a benzofused ring;

(b) 4- to 12-membered bicyclic-heterocyclic rings wherein 1 to 6 ring atoms are independently selected from nitrogen, oxygen and sulfur wherein said bicycle-heterocyclic rings are optionally substituted with 1 to 6 substituents independently selected from the group consisting of halo; hydroxy; $(C_1-C_4)$alkyl optionally substituted with 1 to 3 substituents independently selected from halo, hydroxy, $(C_1-C_3)$alkyl-$SO_2NH_2$— and $NH_2C(=O)NH$—; $(C_1-C_4)$alkoxy optionally substituted with 1 to 3 halo; $(C_1-C_4)$alkyl-CO—; aryl optionally substituted with 1 to 3 substituents independently selected from halo, $(C_1-C_4)$alkyl optionally substituted with 1 to 3 halo and $(C_1-C_4)$alkoxy; benzyl optionally substituted with 1 to 3 substituents independently selected from halo, $(C_1-C_4)$alkyl optionally substituted with 1 to 3 halo and $(C_1-C_4)$alkoxy; —CHO; cyano; $(C_1-C_4)$alkyl-CO—; $NH_2$—CO—; $NH_2$—$CH_2$—; amino; $(C_1-C_4)$alkyl-NH—; di-[$(C_1-C_4)$alkyl]N—; $(C_1-C_4)$alkyl-CO—NH—; $(C_1-C_4)$alkyl-NH—CO—; hydrazino; azido; ureido; amidino; guanidino; oxo and =N—OH, wherein the optionally substituted $(C_1-C_4)$alkyl are attached to the carbon or nitrogen atoms and other substituents are attached to the carbon atoms in the bicyclic-heterocyclic ring; with the proviso that said bicyclic-heterocyclic ring is not a benzofused ring;

(c) 5- to 17 membered spirocarbocyclic rings wherein said spirocarbocyclic rings are optionally substituted with 1 to 6 substituents independently selected from the group consisting of halo; hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—; phenyl; benzyl; —CHO; cyano; $(C_1-C_4)$alkyl-CO—; $NH_2$—CO—; $NH_2$—$CH_2$—; amino; $(C_1-C_4)$alkyl-NH—; di[$(C_1-C_4)$alkyl ]-N—; $(C_1-C_4)$alkyl-CO—NH—; $(C_1-C_4)$alkyl-NH—CO—; hydrazino; azido; ureido; amidino; guanidino; oxo and =N—OH;

(d) 5- to 17-membered spiroheterocyclic rings wherein 1 to 6 ring atoms are independently selected from nitrogen, oxygen and sulfur, wherein said spiroheterocyclic rings are optionally substituted with 1 to 6 substituents independently selected from the group consisting of halo; hydroxy; $(C_1-C_4)$alkyl optionally substituted with 1 to 3 halo; $(C_1-C_4)$alkyl optionally substituted with 1 to 3 halo; $(C_1-C_4)$alkyl-CO—; phenyl; benzyl; —CHO; cyano; $(C_1-C_4)$alkyl-CO —; $NH_2$—CO—; $NH_2$—$CH_2$—; amino; $(C_1-C_4)$alkyl-NH—; di[$(C_1-C_4)$alkyl ]-N—; $(C_1-C_4)$alkyl-CO—NH—; $(C_1-C_4)$alkyl-NH—CO—; hydrazino; azido; ureido; amidino; guanidino; oxo and =N—OH; and $Z^1$, $Z^2$, $Z^3$ and $Z^4$ are independently selected from the group consisting of hydrogen, halo, $(C_1-C_4)$alkyl optionally substituted with 1 to 3 halo; $(C_1-C_4)$alkyl optionally substituted with 1 to 3 halo; $(C_1-C_4)$alkylsulfonyl; $(C_1-C_4)$alkyl-CO—; carboxy; $(C_1-C_4)$alkyl-COO—; amino; $NH_2CO$—; $(C_1-C_4)$alkyl-CO—NH—; $(C_1-C_4)$alkyl-$SO_2$—NH—; phenyl and naphthyl.

2. A compound according to claim 1 or a salt thereof, wherein $R^1$ is $(C_3-C_{11})$cycloalkyl, wherein said cycloalkyl is partially saturated, fully saturated or fully unsaturated and is optionally substituted with 1 to 3 substituents independently selected from the group consisting of halo, hydroxy, $(C_1-C_5)$alkyl and $(C_3-C_7)$cycloalkyl;

A is attached to the same carbon atom of $R^1$, that is also attached to the nitrogen atom of the piperidine ring, and is selected from the group consisting of $(C_1-C_7)$alkyl optionally substituted with 1 to 3 halo; $(C_2-C_5)$alkenyl; $(C_2-C_5)$alkynyl; hydroxy-$(C_1-C_4)$alkyl; $(C_1-C_4)$alkoxy-(C=O); aryl optionally substituted with 1 to 3 substituents; and an aromatic or non-aromatic heterocyclic ring comprising four to six ring atoms wherein one to two ring atoms are independently selected from nitrogen, oxygen and sulfur and said aromatic or non-aromatic heterocyclic ring is optionally substituted with 1 to 3 substituents; and the substituents said aryl or heterocyclic wherein each of said is optionally substituted with 1 to 3 substituents, and the substituents attached to said aryl or heterocyclic ring are independently selected from halo; $(C_1-C_4)$alkyl optionally substituted with 1 to 3 halo; $(C_1-C_4)$alkoxy optionally substituted with 1 to 3 halo; $(C_1-C_4)$alkyl-CO—; $NH_2$—CO—; $NH_2$—$CH_2$—; amino; $(C_1-C_4)$alkyl-NH—; di[$(C_1-C_4)$alkyl]-N—; $(C_1-C_4)$alkyl-CO—NH— and $(C_1-C_4)$alkyl-NH—CO—;

M is selected from group consisting of a covalent bond, $CH_2$, O, S, $SO_2$, CO, NH, N, [$(C_1-C_6)$alkyl]CONH and NHCO;

Y is selected from the following:

(a) bicyclic rings represented by formula Y1;

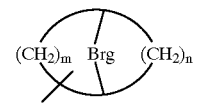

Y1 wherein m and n are independently 1, 2, 3 or 4; Brg is selected from $(CH_2)_p$ wherein p is 0, 1 or 2, and N—$(C_1-C_4)$alkyl; and Y1 is optionally substituted with 1 to 4 substituents independently selected from the group consisting of hydroxy; $(C_1-C_4)$alkoxy optionally substituted with 1 to 3 halo; $(C_1-C_4)$alkyl optionally substituted with 1 to 3 halo; $(C_1-C_4)$alkyl-CO—; phenyl; benzyl; $(C_1-C_4)$alkyl-CO—; $NH_2$—CO—; $NH_2$—$CH_2$—; amino; $(C_1-C_4)$alkyl-NH—; di[$(C_1-C_4)$alkyl]-N—; $(C_1-C_4)$alkyl-CO—NR—; $(C_1-C_4)$alkyl-NH—CO—; oxo and =N—OH;

(b) 6- to 10-membered bicyclic-heterocyclic rings, containing 1 to 4 hetero atoms in the ring, represented by formula Y2, Y3 or Y4:

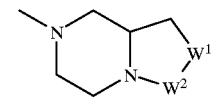

Y2

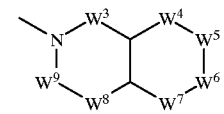

Y3

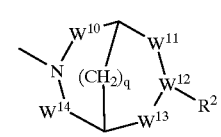

Y4 wherein $W^1$ is selected from $CH_2$, $CH_2CH_2$, O, S and NH;

$W^2$ is selected from $C_2$, O, S, NH and C=O;

$W^3$ is selected from a covalent bond, $CH_2$, O, S, NH and C(=O)—NH;

$W^4$ is selected from a covalent bond, $CH_2$, O, S and NH;

$W^5$ is selected from a covalent bond, $CH_2$, $CH(CH_2OH)$, $CH(CH_2NHSO_2CH_3)$, $CH(CH_2NHC(=O)NH_2)$, $CH_2CH_2$, O, S, NH and C(=O);

$W^6$ is selected from $CH_2$, O, S, NH and N;

$W^7$ is selected from a covalent bond, $CH_2$, O, S, NH and C(=O);

$W^8$ is selected from a covalent bond, $CH_2$, O, S and NH;

$W^9$ is selected from a covalent bond, $CH_2$, O, S, NH $CH_2CH_2$ and C(=O);

$W^{10}$, $W^{11}$, $W^{13}$ and $W^{14}$ are independently selected from covalent bond, $CH_2$, O, S, and NH;

$W^{12}$ is selected from CH and N;

q is 1 or 2; and $R^2$ is selected from hydrogen, $(C_1-C_4)$alkyl and amino; and said bicyclic-heterocyclic rings of formula Y2, Y3 or Y4 is optionally substituted with 1 to 4 substituents independently selected from the group consisting of halo; hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—; aryl optionally substituted with 1 to 3 substituents independently selected from halo, $(C_1-C_4)$alkyl optionally substituted with 1 to 3 halo and $(C_1-C_4)$alkoxy; benzyl optionally substituted with 1 to 3 substituents independently selected from halo, $(C_1-C_4)$alkyl optionally substituted with 1 to 3 halo and $(C_1-C_4)$alkoxy; —CHO; cyano; $(C_1-C_4)$alkyl-C)O—; $NH_2$—CO—; $NH_2$—$CH_2$—; amino; $(C_1-C_4)$alkyl-NH—; di[$(C_1-C_4)$alkyl ]-N—; $(C_1-C_4)$alkyl-CO—NH—; $(C_1-C_4)$alkyl-NH—CO—;oxo and =N—OH;

(c) spirocarbocyclic rings represented by formula Y5:

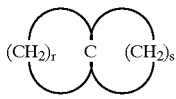

Y5 wherein r and s are independently 2,3,4 or 5; and said spirocarbocyclic ring or formula Y5 is optionally substituted with 1 to 4 substituents independently selected from the group consisting of hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—phenyl; benzyl; $(C_1-C_4)$alkyl-CO—; $NH_2$—CO—; $NH_2$—$CH_2$—; amino; $(C_1-C_4)$alkyl-NH—; di[$(C_1-C_4)$alkyl ]-N—; $(C_1-C_4)$alkyl-CO—NH—; $(C_1-C_4)$alkyl-NH—CO—; oxo and =N—OH; and either of monocyclic carbocyclic ring in Y5 is optionally fused to a benzene or $(C4-C_6)$carbocyclic ring;

(d) 10- to 15-membered spiroheterocyclic rings, containing 1 to 4 hetero atoms in the ring, represented by formula Y6:

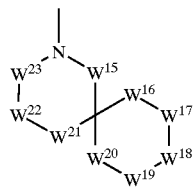

Y6 wherein $W^{15}$, $W^{16}$, $W^{17}$, $W^{18}$, $W^{19}$, $W^{20}$ and $W^{23}$ are independently selected from the group consisting of a covalent bond $CH_2$, O, S and NH;

$W^{21}$ is selected from the group consisting of a covalent bond $CH_2$, O, S, NH and N;

$W^{22}$ is selected from the group consisting of a covalent bond $CH_2$, O, S, NH and C(=O); said spiroheterocyclic ring of formula Y6 is optionally substituted with 1 to 4 substituents independently selected from the group consisting of halo; hydroxy; $(C_1-C_4)$alkyl optionally substituted with 1 to 3 halo; $(C_1-C_4)$alkoxy optionally substituted with 1 to 3 halo; $(C_1-C_4)$alkyl-CO—; phenyl; benzyl; —CHO; cyano; $(C_1-C_4)$alkyl-CO—; $NH_2$—CO—; $NH_2$—$CH_2$—; amino; $(C_1-C_4)$alkyl-NH—; di[$(C_1-C_4)$alkyl]-N—; $(C_1-C_4)$alkyl-CO—NH—; $(C_1-C_4)$alkyl-NH—CO—; hydrazino; azido; ureido; amidino; guanidino; oxo and =N—OH; and optionally fused to a cyclohexane, ben.zene or pyridine ring; and $Z^1$, $Z^2$, $Z^3$ and $Z^4$ are independently selected from the group consisting of hydrogen and halo.

3. A compound according to claim 2 or a salt thereof, wherein $R^1$ is selected from the group consisting of $(C_3-C_{11})$ cycloalkyl;

A is attached to the carbon atom of $R^1$, which is attached to the nitrogen atom of the piperidine ring, and selected from the group consisting of $(C_1-C_7)$alkyl, hydroxy-$(C^1-C_2)$alkyl, $(C_1-C_4)$alkoxy-(C=O), $(C_2-C_5)$alkenyl, phenyl and naphthyl;

M is selected from the group consisting of a covalent bond, $CH_2$, O, $SO_2$, CO, NH, N[$(C_1-C_6)$alkyl], and NHCO;

Y is selected from bicyclic rings represented by formula Y1; 6- to 10-membered bicyclic-heterocyclic rings, containing 1 to 4 hetero atoms in the ring, represented by formula Y2, Y3 and Y4; and 10- to 15-membered spiroheterocyclic rings, containing 1 to 4 hetero atoms in the ring, represented by formula Y6:

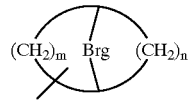

Y1

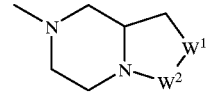

Y2

-continued

Y3

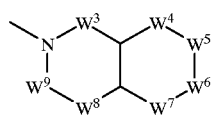

Y4

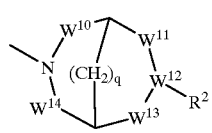

Y6

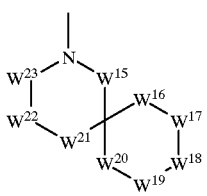

wherein
m and n are independently 1, 2, 3 or 4;
Brg is N—($C_1$–$C_4$)alkyl;
$W^1$ is selected from $CH_2$, $CH_2CH_2$, O and NH;
$W^2$ is selected from $CH_2$ and C=O;
$W^3$ is selected from a covalent bond, $CH_2$ and C(=O)—NH;
$W^4$ is selected from a covalent bond, $CH_2$ and O;
$W^5$ is selected from a covalent bond, $CH_2$, $CH(CH_2OH)$, $CH(CH_2NHSO_2CH_3)$, $CH(CH_2NHC(=O)NH_2)$, $CH_2CH_2$ and C(=O);
$W^6$ is selected from $CH_2$, NH and N[($C_1$–$C_4$)alkyl];
$W^7$ is selected from a covalent bond, $CH_2$ and C(=O);
$W^8$ is selected from a covalent bond and $CH_2$;
$W^9$ is selected from a covalent bond, $CH_2$, $CH_2CH_2$ and C(=O);
$W^{10}$, $W^{11}$, $W^{13}$ and $W^{14}$ are independently selected from a covalent bond and $CH_2$;
$W^{12}$ is selected from CH and N;
q is 1 or 2;
$R^2$ is selected from hydrogen, ($C_1$–$C_4$)alkyl and amino;
$W^{15}$, $W^{16}$, $W^{17}$, $W^{18}$, $W^{19}$, $W^{20}$ and $W^{23}$ are independently selected from the group consisting of a covalent bond and $CH_2$;
$W^{21}$ is selected from the group consisting of a covalent bond $CH_2$, NH and N[($C_1$–$C_4$)alkyl];
$W^{22}$ is selected from the group consisting of a covalent bond $CH_2$ and C(=O);
said group of formula of Y2, Y3 or Y4 is optionally substituted with 1 to 4 substituent independently selected from the group consisting of ($C_1$–$C_4$)alkyl; aryl optionally substituted with 1 to 3 substituents independently selected from halo, ($C_1$–$C_4$)alkyl optionally substituted with 1 to 3 halo and ($C_1$–$C_4$)alkoxy; and benzyl optionally substituted with 1 to 3 substituents independently selected from halo, ($C_1$–$C_4$)alkyl optionally substituted with 1 to 3 halo and ($C_1$–$C_4$)alkoxy; and
said group of formula Y6 is optionally fused to a cyclohexane, benzene or pyridine ring; and optionally substituted with 1 to 4 substituents independently selected from the group consisting of ($C_1$–$C_4$)alkyl, ($C_1$–$C_4$)alkoxy and aryl;

$Z^1$ and $Z^2$ are independently selected from the group consisting of hydrogen and halo; and $Z^3$ and $Z^4$ are both hydrogen.

4. A compound according to claim 3 or a salt thereof, wherein $R^1$ is ($C_6$–$C_{10}$)cycloalkyl;

A is attached to the carbon atom of $R^1$, which is attached to the nitrogen atom of the piperidine ring, and is selected from the group consisting of ($C_1$–$C_7$)alkyl and, phenyl 1;

M is selected from group consisting of a covalent bond, $CH_2$, O, $SO_2$, CO, NH, N[($C_1$–$C_6$)alkyl]and NHCO, Y is selected from:

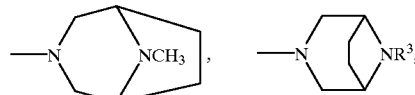

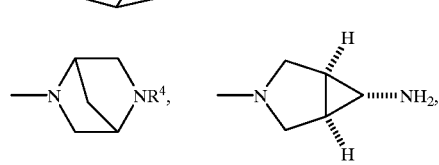

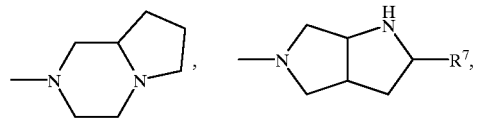

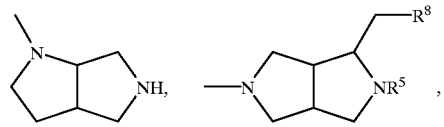

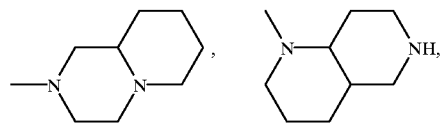

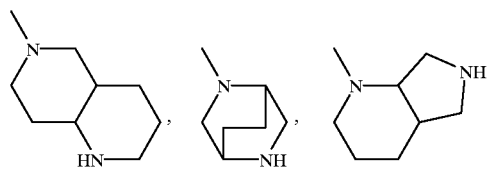

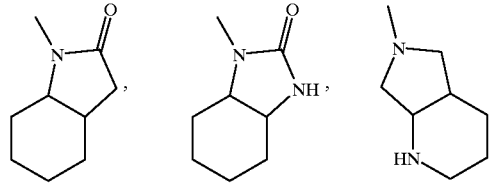

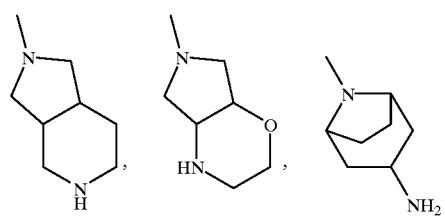

-continued

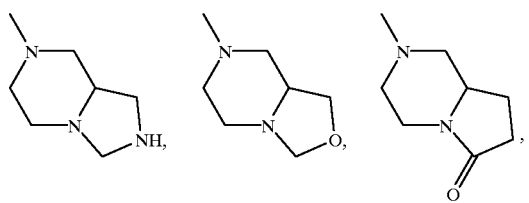

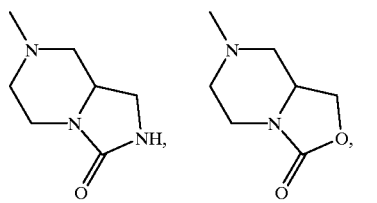

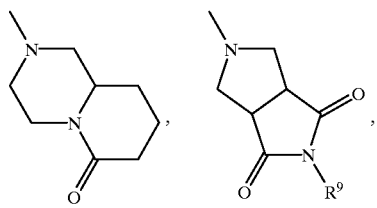

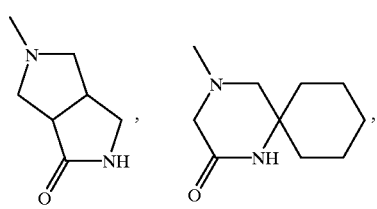

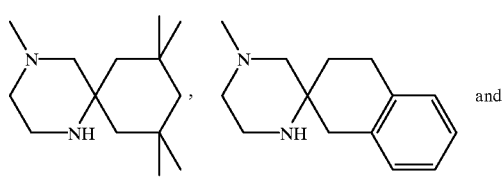

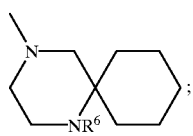

wherein $R^3$, $R^4$, $R^5$, $R^6$, $R^7$ and $R^9$ are independently selected from he group consisting of hydrogen and $(C_1-C_4)$alkyl;

$R^8$ is selected from the group consisting of hydroxy, $NHSO_2CH_3$ and $NHC(=O)NH_2$; and $Z^1$, $Z_2$, $Z^3$ and $Z^4$ are all hydrogen.

5. A compound according to claim 4 or a salt thereof, wherein $R^1$ is $(C_7-C_9)$cycloalkyl;

A is attached to the carbon atom of $R^1$, which is attached to the nitrogen atom of the piperidine ring, and is selected from the group consisting of methyl and phenyl;

M is selected from group consisting of a covalent bond, $CH_2$, O, CO, NH, $N[(C_1-C_6)alkyl]$ and NHCO, Y is selected from:

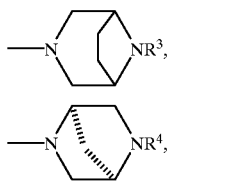

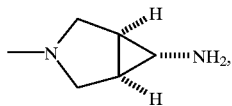

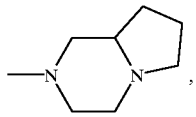

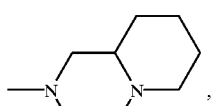

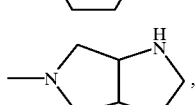

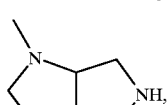

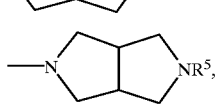

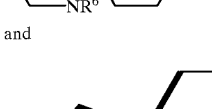

and

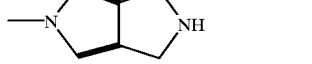

wherein $R^3$, $R^4$, $R^5$ and $R^6$ are independently selected from the group consisting of hydrogen and $(C_1-C_4)$ alkyl; and $Z^1$, $Z^2$, $Z^3$ and $Z^4$ are all hydrogen.

6. A compound according to claim 1 selected from

4- {1-[1-methylcyclooctyl)-4-piperidinyl]-1H-benzimidazole-2-yl}1,4-diazaspiro[5,5]undecane;

2-hexahydropyrrolo[3,4c]pyrrol-2(1H)-yl-1-[1-(1-methylcyclooctyl)-4-piperidinyl]-1H-benzimidazole;

2-(3,8-Diazabicyclo[3,2,1]oct-3-yl)-[1-(1-methylcyclooctyl)-4-piperidinyl]-1H-benzimidazole; and N-[(1SR, 3aRS, 6aSR)-5-{1-[1-Methylcyclooctyl-4-piperidinyl]-1-H-benzimidazol-2-yl}octahydropyrrolo[3,4-c]pyrrole-1-ylmethyl]urea; and a salt thereof.

7. A method for treating a disorder or condition in a mammal, where the disorder or condition is selected from the group consisting of neuropathic pain, inflammation-related hyperalgesia, anxiety, stress disorders or for anesthetizing a mammal or enhancing analgesic function in a mammal comprising administering to said mammal an effective amount of a compound of claim 1 or a pharmaceutically acceptable salt thereof and a pharmaceutically acceptable carrier.

8. A pharmaceutical composition comprising an amount of a compound according to claim 1, or pharmaceutically acceptable salt thereof, and a pharmaceutically acceptable carrier.

* * * * *